US012011146B2

(12) United States Patent
Christensen

(10) Patent No.: US 12,011,146 B2
(45) Date of Patent: Jun. 18, 2024

(54) METHOD OF ASSEMBLY OF AN ENDOSCOPE CONTROL SYSTEM

(71) Applicant: AMBU A/S, Ballerup (DK)

(72) Inventor: Martin Johst Christensen, Copenhagen (DK)

(73) Assignee: AMBU A/S, Ballerup (DK)

( * ) Notice: Subject to any disclaimer, the term of this patent is extended or adjusted under 35 U.S.C. 154(b) by 110 days.

(21) Appl. No.: 17/239,372

(22) Filed: Apr. 23, 2021

(65) Prior Publication Data

US 2021/0338049 A1    Nov. 4, 2021

(30) Foreign Application Priority Data

Apr. 30, 2020   (EP) ..................................... 20172237
Apr. 30, 2020   (EP) ..................................... 20172238

(51) Int. Cl.
*A61B 1/00*      (2006.01)
*A61B 1/005*     (2006.01)
(Continued)

(52) U.S. Cl.
CPC .......... *A61B 1/0052* (2013.01); *A61B 1/0011* (2013.01); *A61B 1/0057* (2013.01); *B29C 65/58* (2013.01); *B29L 2031/753* (2013.01)

(58) Field of Classification Search
CPC ... A61B 1/0052; A61B 1/0011; A61B 1/0057; A61B 1/00006; A61B 1/00;
(Continued)

(56) References Cited

U.S. PATENT DOCUMENTS 3,610,231 A    10/1971   Takahashi
4,207,873 A     6/1980   Kruy
(Continued)

FOREIGN PATENT DOCUMENTS

EP    0306723 B1    3/1993
EP    0754429 B1    9/2004
(Continued)

OTHER PUBLICATIONS

EBay listing, steinelager.de, Wheel 32 x 64 Conical with Spikes and Inner 48 Tooth Gear 64712—Black, available at https://steinelager.de/en/category/7/wheel and https://www.steinelager.de/en/color/26/black, website copyright 2016-1029.
(Continued)

*Primary Examiner* — Timothy J Neal
*Assistant Examiner* — James Edward Boice
(74) *Attorney, Agent, or Firm* — Faegre Drinker Biddle & Reath LLP

(57) ABSTRACT

A method of assembly of an endoscope control system including: holding a first control wheel unit in a position; moving a second control wheel unit in an assembly direction to position the second control wheel unit on the first control wheel unit; moving a housing frame in the assembly direction to position the housing frame on the second control wheel unit; moving a second shaft unit in the assembly direction so that a second shaft is positioned to extend through the connection hole of the housing frame and snaps into engagement with the second control wheel unit; and moving a first shaft unit in the assembly direction so that a first shaft is positioned through the second shaft and snaps into engagement with the first control wheel unit.

22 Claims, 7 Drawing Sheets

(51) Int. Cl.
  *B29C 65/58* (2006.01)
  *B29L 31/00* (2006.01)
(58) Field of Classification Search
  CPC . A61B 1/00105; A61B 1/00066; B29C 65/58;
                                          A61M 25/0136
  USPC ................................................. 600/131, 147
  See application file for complete search history.

(56) References Cited

U.S. PATENT DOCUMENTS

| | | |
|---|---|---|
| 4,461,282 A | 7/1984 | Ouchi et al. |
| 4,473,301 A | 9/1984 | Namyslo |
| 4,617,914 A | 10/1986 | Ueda |
| 4,825,850 A | 5/1989 | Opie et al. |
| 4,924,852 A | 5/1990 | Suzuki et al. |
| 4,942,866 A | 7/1990 | Usami |
| 5,014,685 A | 5/1991 | Takahashi |
| 5,086,200 A | 2/1992 | Kline et al. |
| 5,174,276 A | 12/1992 | Crockard |
| 5,269,202 A | 12/1993 | Kiyosawa et al. |
| 5,329,887 A | 7/1994 | Ailinger et al. |
| 5,426,992 A | 6/1995 | Morii et al. |
| 5,464,007 A | 11/1995 | Krauter et al. |
| 5,507,717 A | 4/1996 | Kura et al. |
| 5,512,035 A | 4/1996 | Konstorum et al. |
| 5,575,755 A | 11/1996 | Krauter et al. |
| 5,871,441 A | 2/1999 | Ishiguro et al. |
| 5,888,192 A | 3/1999 | Heimberger |
| 6,288,351 B1 | 9/2001 | Bruntz |
| 6,599,265 B2 | 7/2003 | Bon |
| 6,656,111 B2 | 12/2003 | Fujii et al. |
| 6,673,012 B2 | 1/2004 | Fujii et al. |
| 6,821,282 B2 | 11/2004 | Perry et al. |
| 7,510,107 B2 | 3/2009 | Timm et al. |
| 7,588,176 B2 | 9/2009 | Timm et al. |
| 7,633,837 B2 | 12/2009 | Daout |
| 7,731,072 B2 | 6/2010 | Timm et al. |
| 7,735,396 B2 | 6/2010 | Ishikawa et al. |
| 7,926,379 B2 | 4/2011 | Gutmann et al. |
| 8,042,423 B2 | 10/2011 | Bannier et al. |
| 8,048,025 B2 | 11/2011 | Barenboym et al. |
| 8,052,636 B2 | 11/2011 | Moll et al. |
| 8,257,303 B2 | 9/2012 | Moll et al. |
| 8,286,845 B2 | 10/2012 | Perry et al. |
| 8,302,507 B2 | 11/2012 | Kanai |
| 8,578,808 B2 | 11/2013 | Koitabashi |
| 8,808,168 B2 | 8/2014 | Ettwein et al. |
| 8,845,521 B2 | 9/2014 | Maruyama |
| 8,904,894 B2 | 12/2014 | Geiser |
| 8,911,362 B2 | 12/2014 | Kaneko |
| 9,044,135 B2 | 6/2015 | Ishii et al. |
| 9,044,138 B2 | 6/2015 | Sjostrom et al. |
| 9,057,421 B2 | 6/2015 | Ishikawa et al. |
| 9,155,865 B2 | 10/2015 | Golden et al. |
| 9,237,837 B2 | 1/2016 | Omoto et al. |
| 9,360,098 B2 | 6/2016 | Roopnarine |
| 9,394,985 B2 | 7/2016 | Kobayashi et al. |
| 9,457,168 B2 | 10/2016 | Moll et al. |
| 9,534,681 B2 | 1/2017 | Ishikawa |
| 9,545,253 B2 | 1/2017 | Worrell et al. |
| 9,833,131 B2 | 12/2017 | Golden et al. |
| 9,949,623 B2 | 4/2018 | Lang et al. |
| 10,085,623 B2 | 10/2018 | Osaki |
| 10,197,153 B2 | 2/2019 | Dumanski et al. |
| 10,203,022 B2 | 2/2019 | Atmur et al. |
| 10,238,271 B2 | 3/2019 | Haraguchi |
| 11,786,112 B2 | 10/2023 | Nielsen et al. |
| 2001/0037051 A1 | 11/2001 | Fujii et al. |
| 2002/0019591 A1 | 2/2002 | Bon |
| 2002/0094232 A1 | 7/2002 | Lipp et al. |
| 2002/0099266 A1 | 7/2002 | Ogura et al. |
| 2004/0010245 A1 | 1/2004 | Cerier et al. |
| 2004/0015054 A1* | 1/2004 | Hino .................. G02B 23/2476 600/146 |
| 2009/0149709 A1 | 6/2009 | Koitabashi |
| 2009/0247828 A1 | 10/2009 | Watanabe et al. |
| 2011/0118550 A1 | 5/2011 | Tulley |
| 2011/0144440 A1 | 6/2011 | Cropper et al. |
| 2011/0208001 A1 | 8/2011 | Haeckl et al. |
| 2012/0277535 A1 | 11/2012 | Hoshino |
| 2013/0204096 A1 | 8/2013 | Ku et al. |
| 2013/0296848 A1* | 11/2013 | Allen, IV ........... A61B 18/1445 606/41 |
| 2014/0058323 A1 | 2/2014 | Hoshino |
| 2014/0142389 A1 | 5/2014 | Lim et al. |
| 2014/0296640 A1* | 10/2014 | Hoshino .............. A61B 1/0052 600/146 |
| 2014/0343489 A1 | 11/2014 | Lang et al. |
| 2015/0057537 A1 | 2/2015 | Dillon et al. |
| 2015/0359415 A1 | 12/2015 | Lang et al. |
| 2016/0067457 A1 | 3/2016 | Selkee |
| 2018/0132899 A1 | 5/2018 | SooHoo |
| 2019/0029498 A1 | 1/2019 | Mankowski et al. |
| 2019/0035440 A1 | 1/2019 | Yuan et al. |
| 2019/0209205 A1* | 7/2019 | Nishio ........... A61B 17/320758 |
| 2019/0313884 A1 | 10/2019 | Isobe |
| 2019/0350440 A1 | 11/2019 | Leong et al. |
| 2021/0338050 A1 | 11/2021 | Christensen et al. |
| 2021/0338051 A1 | 11/2021 | Nielsen et al. |

FOREIGN PATENT DOCUMENTS

| | | |
|---|---|---|
| EP | 2594307 A1 | 5/2013 |
| EP | 2692227 A1 | 2/2014 |
| EP | 2692277 A1 | 2/2014 |
| EP | 2594307 B1 | 9/2016 |
| EP | 2692227 B1 | 8/2018 |
| JP | 09-038028 A | 2/1997 |
| JP | 2005-160790 A | 6/2005 |
| WO | 2008/023965 A1 | 2/2008 |
| WO | 2014186519 A2 | 11/2014 |
| WO | 2018/022402 A1 | 2/2018 |
| WO | 2018/022418 A2 | 2/2018 |
| WO | 2018/131305 A1 | 7/2018 |
| WO | 2021213600 A2 | 10/2021 |

OTHER PUBLICATIONS

Extended European Search Report issued in EP20172237.8, dated Oct. 19, 2020, 9 pages.
Extended European Search Report issued in EP20172238.6, dated Oct. 26, 2020, 9 pages.
Extended European Search Report issued in EP20172242.8, dated Oct. 12, 2020, 8 pages.
Industrial conical gear, cogwheel, available at Dreamstime.com, website copyright 2000-2019.
Jain et al., "Micromanipulator: Effectiveness in Minimally Invasive Neurosurgery," Minim Invasive Neurosurg 2003; 46(4): 235-239.
Jarrahy et al., "A new powered endoscope holding arm for endoscopic surgery of the cranial base," Minim Invasive Neurosurg 2002, 45(3): 189-192.
Lerner, "A Passive Seven Degree of Freedom Postitioning Device for Surgical Robots and Devices," dissertation submitted to the Johns Hopkins University, Baltimore, Maryland, 1998.
Poels, Design of the Frame and Arms of a Master for Robotic Surgery, Traineeship report, Technische Universiteit Eindhoven, Department of Mechanical Engineer, Control Systems Technology Group, Jul. 2007.
Office Action in related U.S. Appl. No. 17/241,882 dated Dec. 23, 2022, 12 pages.
Office Action in related U.S. Appl. No. 17/239,373 dated Jul. 21, 2023, 23 pages.
Office Action received for European Patent Application No. 20172237.8 dated Jan. 22, 2024, 5 pages.
Office Action received for European Patent Application No. 20172238.6 dated Jan. 16, 2024, 5 pages.

(56) References Cited

OTHER PUBLICATIONS

Final Office Action received for U.S. Appl. No. 17/239,373 dated Mar. 14, 2024, 24 pages.

* cited by examiner

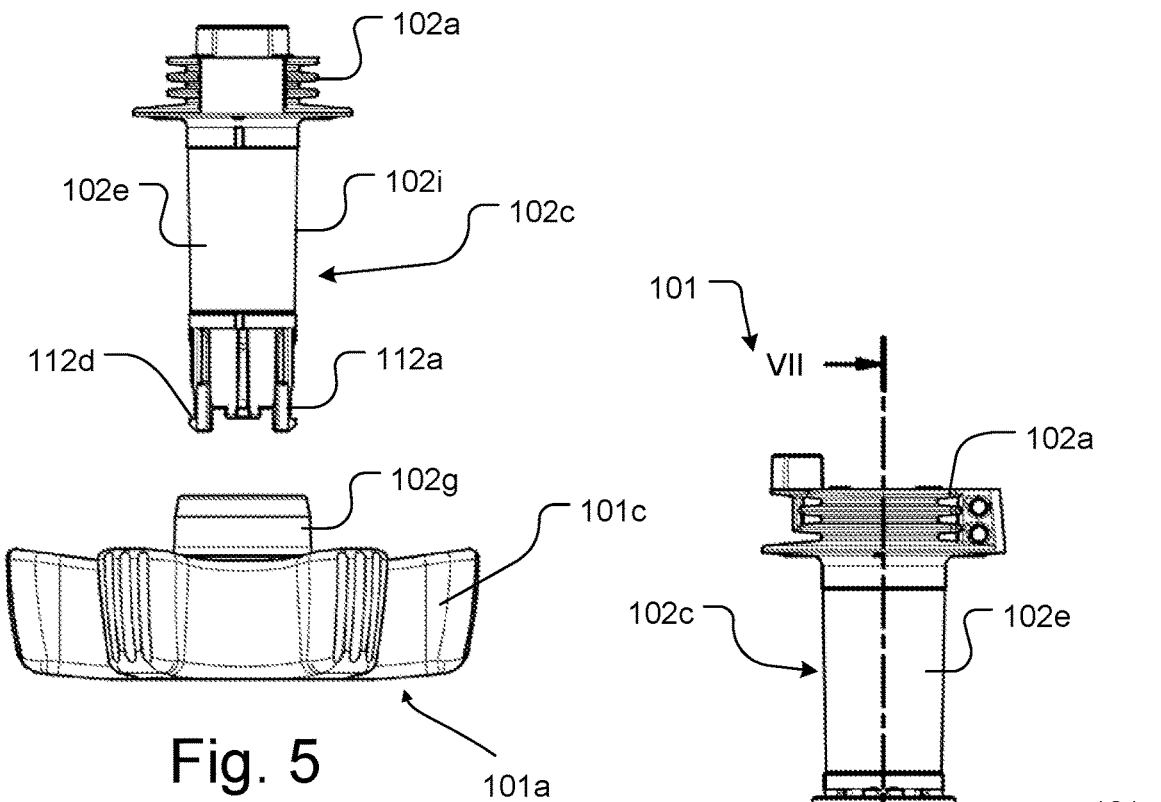
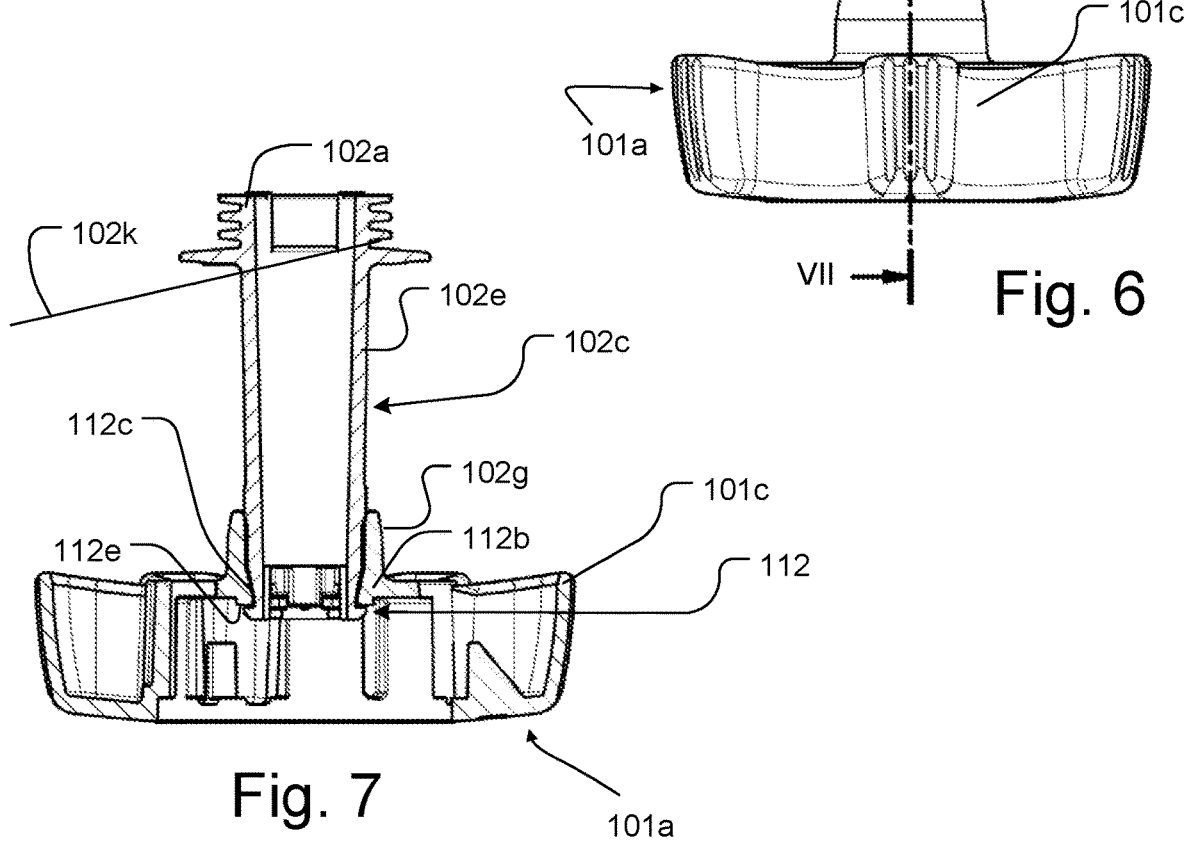

METHOD OF ASSEMBLY OF AN ENDOSCOPE CONTROL SYSTEM

CROSS-REFERENCE TO RELATED APPLICATIONS

The present application claims priority to and the benefit of European Patent Application Nos. 20172237.8 and 20172238.6, filed Apr. 30, 2020, which are incorporated by reference herein in their entirety.

TECHNICAL FIELD

The present disclosure relates to insertable medical vision devices, such as, but not limited to, endoscopes, in particular disposable insertion endoscopes, such as duodenoscopes, gastroscopes, and colonoscopes, and to methods of assembly thereof. More specifically, the present disclosure relates to endoscope control systems comprising control wheels connected to associated wire drums for connection to steering wires, whereby rotation of the control wheels controls a bending operation of a tip of the endoscope, and to assembly of such control systems.

BACKGROUND

Endoscopes are typically equipped with a light source and a vision receptor including a vision or image sensor. Provided that enough light is present, it is possible for the operator to see where the endoscope is steered and to set the target of interest once the tip has been advanced thereto.

Endoscopes typically comprise an elongated insertion tube with a handle at the proximal end, as seen from the operator, and visual inspection means, such as a built-in camera including a vision sensor, at a distal end of the elongated insertion tube. This definition of the terms distal and proximal, i.e. "proximal" being the end closest to the operator and "distal" being the end remote from the operator, as used herein for endoscopes in general, is adhered to in the present specification. Electrical wiring for the camera and other electronics, such as one or more LEDs accommodated in the tip part at the distal end, runs along the inside of the elongated insertion tube from the handle to the tip part. A working or suction channel may run along the inside of the insertion tube from the handle to the tip part, e.g. allowing liquid to be removed from the body cavity or allowing for insertion of surgical instruments or the like into the body cavity. The suction channel may be connected to a suction connector, typically positioned at a handle at the proximal end of the insertion tube.

To be able to maneuver the endoscope inside the body cavity, the distal end of some endoscopes comprises a bendable distal tip, which may be bendable in one, e.g. an up/down dimension, or two dimensions, e.g. an up/down dimension and a left/right dimension. The bendable tip often comprises a bending section with increased flexibility, e.g. achieved by articulated segments of the bending section. The maneuvering of the endoscope inside the body is typically done by tensioning or slacking steering wires also running along the inside of the elongated insertion tube from the tip part through the remainder of articulated segments to a control system or control mechanism positioned in or forming part of the handle.

An endoscope control system for performing a bending operation in two dimensions is known from WO2018022418A2. This control system includes two control wheels connected to associated wire drums for connection to associated steering wires of the endoscope, whereby rotation of the control wheels controls the bending operation in two dimensions.

U.S. Pat. No. 4,461,282 discloses another endoscope control system including two control wheels.

U.S. Pat. No. 5,329,887 discloses another endoscope control system including two control wheels and in which a separately provided snap ring or snap clip attaches a control shaft.

In the prior art, other separate attachment means, such as locking rings or spring clips, have also been applied to attach parts to each other.

Furthermore, the control systems of the prior art are often assembled in a manner which requires flipping the parts around the already assembled parts during the method of assembly.

SUMMARY OF EMBODIMENTS OF THE DISCLOSURE

A first aspect of the present disclosure relates to a method of assembly of an endoscope control system, the endoscope control system being for performing a bending operation in a disposable insertion endoscope,
wherein the endoscope control system comprises:
a housing frame for forming or for forming part of an endoscope handle housing, the housing frame comprising a connection hole;
a first control wheel unit comprising a first wheel handle;
a second control wheel unit comprising a second wheel handle;
a first shaft unit, the first shaft unit comprising a first wire drum and a first shaft, the first shaft connecting the first control wheel unit to the first wire drum, the first wire drum being for connection to a first steering wire of the endoscope, whereby rotation of the first wheel handle relative to the housing frame about an axis of rotation controls the bending operation in a first dimension;
a second shaft unit, the second shaft unit comprising a second wire drum and a second shaft, the second shaft connecting the second control wheel unit to the second wire drum, the second wire drum being for connection to a second steering wire of the endoscope, whereby rotation of the second wheel handle relative to the housing frame about an axis of rotation controls the bending operation in a second dimension;
wherein the method of assembly comprises, in sequence, the steps of:
1) holding the first control wheel unit in a position;
2) moving the second control wheel unit in an assembly direction to position the second control wheel unit on the first control wheel unit;
3) moving the housing frame in the assembly direction to position the housing frame on the second control wheel unit;
4) moving the second shaft unit in the assembly direction so that the second shaft is positioned to extend through the connection hole of the housing frame and snaps into engagement with the second control wheel unit by means of a second snap connection between the second shaft and the second control wheel unit; and
5) moving the first shaft unit in the assembly direction so that the first shaft is positioned to extend through the connection hole of the housing frame and through the second shaft and snaps into engagement with the first control wheel unit by means of a first snap connection between the first shaft and the first control wheel unit;

whereby the first and second control wheel units, the housing frame, and the first and second shaft units are maintained in position relative to each other in the assembly direction by means of the first and second snap connections.

The methods of the present disclosure may allow for mounting and/or positioning all the parts involved, i.e. the first and second control wheel units, the housing frame, and the first and second shaft units from one side only and in one assembly direction only, and/or wherein, in each of the steps 2) to 5), only the next part to be added is moved in one direction only.

The first and second snap connections may ensure that the parts of the control system assembled in steps 1) to 5), and potentially any further steps during or in between steps 1) to 5), are attached to each other only by means of the movement carried out in steps 4) and 5). Accordingly, the movement in each of steps 4) and 5) may activate the snap connections, potentially without any further action being required to activate these.

Furthermore, locking rings or similar separate locking elements as used in the prior art for attaching the first and second control wheel units, the housing frame, and the first and second shaft units can be replaced by the first and second snap connections so that separate locking elements can entirely be avoided in the attachment of these parts to each other. Accordingly, the methods according to the present disclosure may involve that no locking rings and/or separate locking elements are applied during and/or between steps 1) to 5) of the method.

Furthermore, when the parts are assembled in the sequence of steps 1) to 5) in one single assembly direction, flipping around or turning the already assembled parts may be avoided during the sequence of steps 1) to 5).

If a jig as described below is used during the method steps 1) to 5), it is possible to avoid removing the already assembled parts from the jig during steps 1) to 5) and any further steps carried out simultaneously with or in between steps 1) to 5).

Thus, simpler and/or faster assembly of the control system may be achieved with the methods of assembly and control systems according to the present disclosure.

Furthermore, a lower error rate may be achieved, and one or more of or all the method steps can be carried out on a machine, which may further increase the above advantages.

The housing frame may be a first half shell of the handle housing, the handle housing potentially further comprising a second half shell that may be attached to the first half shell after completion of steps 1) to 5). Hereby, the first and second wire drums may be positioned inside the assembled handle housing.

The first and/or second wheel handles may be generally circular and/or comprise finger depressions.

Each of the first and second control wheel units may comprise a central part or wheel sleeve, first and second, respectively, each potentially surrounding a center opening. The central parts may be cylindrical and may extend towards the housing frame in the assembled control system. In the assembled control system, the first central part may extend into the second central part, which may help proper positioning of the control wheel units in relation to each other during assembly. The second central part may extend to encompass part of the first central part in the assembled state of the control system.

The term "cylindrical" as used herein may involve conical or frusto-conical shapes.

The first shaft may comprise a bearing surface, and the second shaft may comprise a bearing surface, these bearing surfaces being for abutment and rotational sliding on associated bearing elements potentially fixed to or in one piece with the housing frame, see further below.

The first and/or second shafts may each be tubular and/or comprise a substantially cylindrical circumferential wall which may provide the associated bearing surfaces. A cross section or diameter of the first shaft may be smaller than that of the second shaft.

The axes of rotation may be coinciding. The first and second shafts, and potentially the first and second control wheel units and/or the first and second wheel handles, may extend coaxially in the assembled control system.

In the assembled control system, the first and second wire drums on one hand and the first and second wheel handles on the other hand may be positioned on opposite sides of the housing frame. The first wire drum may be positioned in extension of the second wire drum and/or farther away from the housing frame than the second wire drum.

The first and second wire drums may be positioned at ends of the first and second shafts, respectively.

The assembled control system may further include an inner bearing element which in a further step before, during, or after step 4) may be moved in the assembly direction to extend through the second shaft unit and/or through the connection hole of the housing frame. In the assembled control system, the inner bearing element may be rotationally fixed to the housing frame. The inner bearing element may comprise an inner bearing surface which may be positioned farther from a common axis of rotation than the outer bearing surface of the first shaft, the inner bearing surface abutting the outer bearing surface so that rotation of the second control wheel unit is at least partly borne on the inner bearing element. The inner bearing element may include a cylindrical and/or tubular inner bearing sleeve having a wall. The inner bearing element may separate rotation of the control wheel units from each other.

The assembled control system may further comprise an outer bearing element which may be in one piece with or fixed to the housing frame. The outer bearing element may surround and/or define the connection hole of the housing frame. The outer bearing element may be tubular and/or cylindrical and may comprise a wall which may extends away from the housing frame in a direction towards the first control wheel unit. The outer bearing element may comprise an inner bearing surface which may be positioned farther from a common axis of rotation than the outer bearing surface of the second shaft, the inner bearing surface abutting the outer bearing surface so that rotation of the second control wheel unit is at least partly borne on the outer bearing element. The outer bearing element may be an outer bearing sleeve that encompasses at least part of the second shaft.

The control system may further include a center shaft which in step 5) or in a further step before or, in particular, after step 5) may be moved in the assembly direction to extend through the connection hole of the housing frame, the first and second shaft units, and the center openings of the first and second control wheel units. The center shaft may comprise or may be attached or fixed to a connector frame, and the connector frame may be attached or fixed to the housing frame after insertion of the center shaft so that the center shaft is fixed to the housing frame. This may provide improved rigidity and structural stability of the assembled control system. The connector frame can be attached or fixed to the housing by one or more snap connections, screws, connector pins, or any other suitable means.

The center shaft may include a center shaft arm or a center shaft frame that extends radially from a shaft part thereof and is to be positioned within the handle housing in the assembled endoscope. Similarly, the inner bearing element may include an inner bearing element arm or an inner bearing element frame that extends radially from a sleeve part thereof and is to be positioned within the handle housing in the assembled endoscope. Each of these arms or frames may be fixed to the housing frame in order to attach or fix the center shaft and/or inner bearing element to the housing frame. This attachment or fixation may be achieved by one or more snap connections, screws, connector pins, or any other suitable means. The inner bearing element arm or frame may be directly attached or fixed to the housing frame, the center shaft arm or frame being directly attached or fixed to the inner bearing element arm or frame so as to be indirectly attached or fixed to the housing frame, in which case the inner bearing element arm or frame may be positioned between the center shaft arm or frame and the housing frame.

When the center shaft has been positioned, a cap may be moved opposite to the assembly direction and be attached at and/or to a tip end of the center shaft. This attachment may involve a further snap connection which may be provided in a manner identical or similar to the first and second snap connections as described herein. Accordingly, the cap may include one or more, such as two, resilient/pushable connection parts, whereas the tip end of the center shaft may include associated one or more connection parts taking the form of, for example, recesses. This snap engagement may similarly be activated during or at the end of the insertion of the center shaft into the control system. The cap may, thus, be positioned and held in the jig described below before or at the same time as the first control wheel unit is positioned in the jig. The cap may cover and/or attach a first brake of the first control wheel unit, see further below regarding the brake. The brake may be encased or housed within a spacing defined by interior surfaces of the first wheel handle and the cap. If the first control wheel handle includes such a brake, it may be advantageous to, instead, remove control system from the jig after steps 1) to 5), then potentially flipping the assembled control system around, e.g. a 180 degrees rotation, after which the first brake is assembled and positioned to form part of the first control wheel unit, after which, again, the cap is positioned as described. Alternatively, the first brake and the cap are mounted to form part of the first control wheel unit before or during step 1). The cap may also be included even if no brake is included in the first control wheel unit; in this case, the cap and associated snap connection may simply be used to attach or hold the tip part of the center shaft.

In the assembled control system, a brake handle for activation of a second brake, which is the brake of the second control wheel unit described further below, may be attached to the housing frame. During the method of assembly, when the second control wheel unit has been positioned in step 2), before step 3), the brake handle may be moved in the assembly direction to be positioned on the second control wheel unit. In step 3), the housing frame may then be attached to the brake handle. This attachment may, again, involve a further snap connection which may be provided in a manner identical or similar to the first and second snap connections as described herein. Accordingly, the housing frame, such as the outer bearing element of the housing frame, may include one or more, such as two, resilient/ pushable connection parts, whereas the brake handle includes associated one or more connection parts taking the form of, for example, projections. This snap engagement may similarly be activated during or at the end of the positioning movement of the housing frame.

In step 1), the first control wheel unit may be positioned in a jig, the jig holding the first control wheel unit, potentially in a fixed position. A jig may be any device suitable for holding at least the first control wheel unit in position during the assembly process.

In step 2), the second control wheel unit is also positioned and held in the jig.

In step 3), the housing frame is also positioned and held in the jig.

The jig may include a jig block with a jig depression shaped to provide a positive engagement with the first control wheel unit, especially the first wheel handle. Similarly, the jig depression may be shaped to also provide a positive engagement with the second control wheel unit, especially the second wheel handle, when the second control wheel unit is positioned on the first control wheel unit in the jig. Similarly, the jig depression may be shaped to also provide a positive engagement with the housing frame or a part thereof when the housing frame is positioned on the second control wheel unit in the jig. Hereby, all of these elements can be maintained in relative positions until the snap connections are engaged in steps 4) and 5).

After steps 1) to 5), the assembled control system may be removed from the jig, and further assembly of the endoscope may occur.

In step 2), the second control wheel unit may be positioned in abutment with the first control wheel unit, or they may be positioned at a distance from each other, a further element potentially providing this distance, or the distance being achieved during the subsequent steps of assembly.

In step 3), the housing frame may be positioned in abutment with the second control wheel unit, or they may be positioned at a distance from each other, a further element potentially providing this distance, or the distance being achieved during the subsequent steps of assembly.

One or both snap connections may be snap fittings.

The second snap connection may axially and/or rotationally fix the second shaft unit to the second control wheel unit. The second snap connection may include one or more, such as two, connection parts of the second shaft unit interlocking with one or more, such as two, associated connection parts of the second control wheel unit. These connection parts may be any suitable mutually engaging snap connection parts. During the movement of the second shaft unit, the one or more connection parts of one of the second shaft unit and the second control wheel may be pushed in a radial direction (inwardly or outwardly) and, then, when the second shaft unit is further moved or inserted, resiliently snap back to engage the associated one or more connection parts. As is conventional, this may be achieved by the one or more of the connection parts that are not pushed including a ramp or an inclined surface, which forces the pushable connection parts in the radial direction during the movement of the second shaft unit. Accordingly, one or more of the pushable connection parts may include a barb surface which during the snap moves into engagement with an associated barb surface of the other connection parts to secure the position of the second shaft unit to the second control wheel unit. For example, the pushable connection parts may be included in the second control wheel unit, potentially in the central part thereof, and the associated connection parts may be included, potentially as simple holes or recesses, in the second shaft unit. The pushable connection part(s) may be provided by two axially extending slots defining a resilient, axially moveable pin between them.

Like the second snap connection, the first snap connection may axially and/or rotationally fix the first shaft unit to the first control wheel unit. And the first snap connection may include one or more, such as two, connection parts of the first shaft unit interlocking with one or more, such as two, associated connection parts of the first control wheel unit. These connection parts may be any suitable mutually engaging snap connection parts. During the movement of the first shaft unit, the one or more connection parts of one of the first shaft unit and the first control wheel may be pushed in a radial direction (inwardly or outwardly) and, then, when the first shaft unit is further moved or inserted, resiliently snap back to engage the associated one or more connection parts. And again, this may be achieved by the one or more of the connection parts that are not pushed including a ramp or an inclined surface, which forces the pushable connection parts in the radial direction during the movement of the first shaft unit. Accordingly, one or more of the pushable connection parts may include a barb surface which during the snap moves into engagement with an associated barb surface of the other connection parts to secure the position of the first shaft unit to the first control wheel unit. For example, the pushable connection parts may be included in the first shaft unit, potentially in the first shaft thereof, and the associated connection parts may be included, potentially as simply holes or recesses, in the first control wheel unit. The pushable connection part(s) may be provided by two axially extending slots defining a resilient, axially moveable pin between them.

Hereby, the first and second snap connections, when engaged, prevent movement of the first and second control wheels, the housing frame, and the first and second shaft units relative to each other in the assembly direction, which may be an axial direction of the control system. Accordingly, the barb surfaces may face in the axial direction. The barbs may be provided as projections extending in a radial direction.

The assembly direction may be parallel with the axes of rotation of the first and second control wheel units.

The housing frame may include one or more screw towers for fastening of the screws described above. The screw towers may extend oppositely to the assembly direction.

In the assembled control system, one of or both the first and second control wheel units may comprise a brake. Activation of the brake may move the brake from a released position to a braking position. A brake force of the brake in the braking position may brake rotation of the associated control wheel unit. The brake force may in the released position be at least partially released. The brake may be a multi-disc brake, which may include a stack of at least three brake discs. Each brake may include a handle or a button, which may activate the brake, e.g. by rotation of the handle or button. Each brake may comprise a spring, which may be a helical spring. Each brake may be assembled in or on the associated control wheel unit or associated wheel handle before or after or during the associated steps of positioning the first and second control wheel units, i.e. steps 1) and 2), respectively. A second such brake may be assembled in the second control wheel unit or the second wheel handle before step 1) or before step 2). A first such brake may be assembled in the first control wheel unit or the first wheel handle after step 4) or after step 5). In case a jig is applied as described above, the method of assembly may include the further step of removing the control system from the jig after step 5). After the step of removing the control system from the jig, the method of assembly may include the further step of assembling the first brake in the first control wheel unit.

The endoscope control system can alternatively be denoted an endoscope bending operation apparatus.

The control system may be positioned on or in, or may form part, of an endoscope handle of the endoscope, see also further below.

The first and/or second control wheel units and/or the inner and/or outer bearing element, and/or the first and/or second shaft units may form part of the endoscope handle for or of an endoscope.

The first control wheel unit may be positioned coaxially with the second control wheel unit and/or with the outer bearing member and/or the inner bearing member, and/or the first and/or second shaft units.

The handle housing may be manufactured of a plastic material, potentially a plastic polymer material and/or an artificial resin. One or both control wheels or at least the sleeves thereof described below, and/or one or both wire drums may be manufactured from one or more plastics or a plastics material, such as POM. The entire control system may be manufactured of one or more plastics or plastic materials or plastic polymer materials or artificial resins, and/or the control system does not include any metal. Any one of the plastic materials mentioned herein may be a plastic polymer material which comprises or consists of one or more of PC, polypropylene (PP), acrylonitrile butadiene styrene (ABS), polyethylene (PE), polyamide (PA), polyurethane (PU), polystyrene (PS), polylactic acid (PLA), polyvinyl chloride (PVC), polyoxymethylene (POM), polyester, polyethylene terephthalate (PET), and acrylic (PMMA). The polymer may be a copolymer of one or more monomers of the latter materials.

Rotation of the control wheel units may occur relative to the housing frame. The handle housing may be a handle shell or a housing shell. The housing frame and/or the handle housing may be manufactured of a rigid material, such as a rigid plastic polymer.

The first and/or second wire drums may be a pulley/pulleys. The first and second steering wires may form part of the control system and may be attached to the first and the second drum, respectively, and/or may be wound up or woundable on these, respectively.

The axis of rotation may be an axis of rotation of also the first and/or second shafts.

The axis of rotation may be a center axis of the first and/or second control wheel units and/or of the first and/or second wheel handles and/or of the first and/or second shaft units and/or shafts and/or of the control system and/or of the outer bearing element and/or of the inner bearing element and/or of the center shaft.

The second wheel handle may be positioned between the handle housing and the first wheel handle. The first shaft unit may extend through the second wheel handle and/or through the second shaft unit, and/or through the second wire drum. The first shaft unit may extend through center holes or center openings of these elements.

The second wire drum may be positioned between the first wire drum and the second control wheel unit.

The first control wheel unit may be an inner control wheel and/or may be positioned closer to the housing frame than the second control wheel unit, and/or may control a bendable tip of the endoscope in an up/down dimension. The second control wheel unit may be an outer control wheel and/or may control a bendable tip of the endoscope in a left/right dimension.

The second shaft may encompass at least part of the first shaft. The first and/or second shafts may each be cylindrical or circular cylindrical and/or may be embodied as cylinder shells and/or may be hollow. The second shaft may be positioned to be coaxial with the first shaft. The inner bearing element may be an inner bearing sleeve and may be the only element positioned between the first shaft and the second shaft.

Any one of or all of the above-mentioned elements of the control system, potentially except for steering wires and/or parts of the potential brakes may be manufactured from plastic polymer(s).

The second control wheel unit may be positioned coaxially with and potentially axially shifted in relation to the first control wheel unit. A diameter or a cross-sectional dimension of the two wheel handles may be different from each other, potentially so that an outer one of the two wheel handles has a smaller diameter or smaller cross-sectional dimension.

The outer bearing element may be in one piece with the housing frame and/or molded in one piece with the handle housing. Alternatively, the outer bearing element is provided separately from and is fixed to the handle housing.

Any one or more of or all steps 1) to 5) may be carried out automatically. Any one or more or all of potential further steps of the method as disclosed above may also be carried out automatically.

A step being carried out automatically may involve that the step is carried out by means of a machine, wherein the machine may be or comprise a robot, which may comprise a robotic arm and a control system. The jig may form part of the machine. The jig may be replaced by a holding or gripping mechanism or hand of a robotic arm.

Alternatively or additionally, any one or more or all of the method steps of the methods according to the present disclosure may carried out manually, such as a person using human hands and/or one or more tools for carrying out the step in question.

A combination of automatic and manual assembly may also be envisioned, wherein any one or more of the steps are carried out automatically as described and the remaining steps are carried out manually as described.

In an embodiment of the methods of assembly according to the present disclosure, all the movements of steps 2) to 5) are carried out from one side only.

Hereby, a need to flip around the already assembled parts during the method of assembly may be avoided.

In another embodiment, in each of steps 2) to 5), all already positioned parts of the control system to be assembled remain in a held position.

In another embodiment, only the movement carried out in steps 4) and 5) affect the attachment of the parts assembled in steps 1) to 5) to each other.

In other words, the first and second snap connections may be the only connections affecting the attachment of the parts to each other. The snap connections may generally activate automatically during and because of the movement in steps 4) and 5).

It is understood that connection parts of the snap connections may also move in themselves, typically in a radial direction, during the snapping action, as described in the above.

In another embodiment, during the sequence of steps 1) to 5), no separate locking device is applied to attach the parts to each other.

In another embodiment, the first and second snap connections are provided only by snap connection parts provided in one piece with the first shaft unit, the first control wheel unit, the second shaft unit, and the second control wheel unit, respectively.

In another embodiment, the first snap connection comprises at least one primary connector part forming part of the first shaft unit and at least one secondary connector part forming part of the first control wheel unit, the primary and secondary connector parts in step 5) snapping directly onto each other to form the first snap connection; and the second snap connection comprises at least one tertiary connector part forming part of the second shaft unit and at least one quaternary connector part forming part of the second control wheel unit, the tertiary and quaternary connector parts in step 4) snapping directly onto each other to form the second snap connection.

Any one or more of the primary to quaternary connection parts may be provided as the pushable/moveable/resilient connection parts described above. The other one of the primary and secondary connection parts and the tertiary and quaternary connection parts, respectively, may then be the static/non-moveable connection parts.

Any one or more of or all the connection parts may include a ramp facilitating the resilient movement of one or more of the pushable connection parts during the steps 4) and/or 5).

In another embodiment, no further steps are involved in the method during the sequence of steps 1) to 5).

In another embodiment, before step 1), the first wheel is positioned in a jig, the first wheel being held in the jig in step 1) and during the sequence of steps 2) to 5).

The method may, generally, further comprise the step of, after step 5), removing the parts assembled in steps 1) to 5) from the jig.

In another aspect, the present disclosure involves an endoscope control system for performing a bending operation in a disposable insertion endoscope, wherein the endoscope control system comprises:

a housing frame for forming or for forming part of an endoscope handle housing, the housing frame comprising a connection hole;

a first control wheel unit comprising a first wheel handle;

a second control wheel unit comprising a second wheel handle;

a second shaft unit, the second shaft unit comprising a second wire drum and a second shaft, the second shaft connecting the second control wheel unit to the second wire drum, the second wire drum being for connection to a second steering wire of the endoscope, whereby rotation of the second wheel handle relative to the housing frame about an axis of rotation controls the bending operation in a second dimension;

wherein the second control wheel is positioned between the first control wheel and the housing frame, the second shaft extends through the connection hole of the housing frame, and the first shaft extends through the connection hole of the housing frame and through the second shaft; and wherein the first shaft is connected to the first control wheel unit by means of a first snap connection between the first shaft and the first control wheel unit, and the second shaft is connected to the second control wheel unit by a second snap connection between the second shaft and the second control wheel unit, whereby the first and second snap connections attach the first and second control wheels, the housing frame, and the first and second shaft units to each other.

The control system according to the present aspect may include any one or more of the embodiments and/or structural features disclosed above in relation to the control systems assembled according to the methods of the present disclosure.

In an embodiment of the control system according to the present aspect, the first and second snap connections maintain attachment between the first and second control wheels, the housing frame, and the first and second shaft units if all other parts are removed.

In another embodiment, the first and second snap connections are provided only by snap connection parts provided in one piece with the first shaft unit, the first control wheel unit, the second shaft unit, and the second control wheel unit, respectively.

In another embodiment, the endoscope control system has been assembled according to the method of any one of the above embodiments of methods of assembly.

In another aspect, the present disclosure involves an endoscope comprising the control system assembled according to any one or more of the above embodiments of methods of assembly and/or comprising the control system according to any one or more of the above embodiments.

In an embodiment of the endoscope according to the present aspect, the endoscope further comprises the first and second steering wires and a distal tip or tip part that comprises a bending section connected to the first and second steering wires so that the control system can activate the bending operation of the bending section via the steering wires.

The endoscope may further comprise an endoscope handle at the proximal end thereof, and/or visual inspection means, such as a built-in camera including a vision sensor, at a distal tip. Electrical wiring for the camera and other electronics, such as one or more LEDs accommodated in the tip part at the distal end, may run along the inside of the elongated insertion tube from the endoscope handle to a PCB or an FPC at the distal tip. A working or suction channel may run along the inside of the insertion tube from the handle to the tip part, e.g. allowing liquid to be removed from the body cavity or allowing for insertion of surgical and/or sampling instruments or the like into the body cavity. The suction channel may be connected to a suction connector, typically positioned at a handle at the proximal end of the insertion tube.

In some embodiments of the endoscope, the endoscope further comprises a distal tip or tip part that comprises a bending section connected to the steering wire(s) so that the control system can activate a bending operation of the bending section via the steering wire(s).

The bending section may be bendable in one or two dimensions, e.g. an up/down dimension and a left/right dimension. The bendable tip may comprise a bending section with increased flexibility, e.g. achieved by articulated segments of the bending section as are known in the art. The steering wire(s) may run along the inside of an elongated insertion tube from the tip through the bending section to the control system positioned in or forming part of the endoscope handle.

The endoscope may be a disposable insertion endoscope. The endoscope may include one or more features as described herein in the above, including the features of endoscopes described in the above introduction to this description, and in connection with the description of the methods and tip parts according to the present disclosure.

The endoscope may comprise an elongated insertion tube with a handle at the proximal end. A tip or tip part may be positioned at the distal end of the elongated insertion tube. The tip may further comprise a bending section positioned between the tip and the elongated insertion tube. The bending section may be configured to be articulated to maneuver the endoscope inside a body cavity.

The endoscope may be a duodenoscope, a gastroscope, or a colonoscope.

An embodiment of the endoscope further comprises the first and second steering wires and a distal tip or tip part that comprises a bending section connected to the first and second steering wires so that the control system can activate the bending operation of the bending section via the steering wires.

A person skilled in the art will appreciate that any one or more of the above aspects of this disclosure and embodiments thereof may be combined with any one or more of the other aspects and embodiments thereof.

BRIEF DESCRIPTION OF THE DRAWINGS

In the following, non-limiting exemplary embodiments will be described in greater detail with reference to the drawings, in which:

FIG. 5 shows an exploded side view of a first control wheel unit and a first shaft unit of the control system of FIG. 1;

FIG. 6 shows an exploded side view of the first control wheel unit and first shaft unit of FIG. 5 in an assembled state and in which the first control wheel unit and first shaft unit have been turned 180 degrees;

FIG. 7 shows a cross section taken along the line VII-VII in FIG. 6;

DETAILED DESCRIPTION

In this disclosure, the term "to accommodate" may additionally or alternatively be defined as "to house" or "to enclose" or "to surround".

In this specification, the terms "integrally" or "integrally provided" or "integrally comprising", "in one piece", or similar may be defined as the associated features forming an integral part of a whole; and/or are in one piece, potentially molded in one piece; and/or are substantially inseparable by hand. When a first element forms part of a second element, this may involve that the first element is provided integrally with or in one piece with the second element.

As mentioned, in this specification, the term "proximal" may be defined as being closest to an operator of the endoscope, and the term "distal" as being remote from the operator. The term "proximal-distal" may be defined as extending between these two extremes, in the present case proximal-distal may extend along a center axis of the tip part extending between a proximal extremity of the proximal end of the tip part and a distal extremity of the distal end of the tip part.

In this specification, an endoscope may be defined as a device adapted for viewing body cavities and/or channels of a human and/or animal body. The endoscope may for instance be a flexible or steerable endoscope. The endoscope may be a duodenoscope or a ureteroscope, a gastroscope, or a colonoscope.

Figure 1:
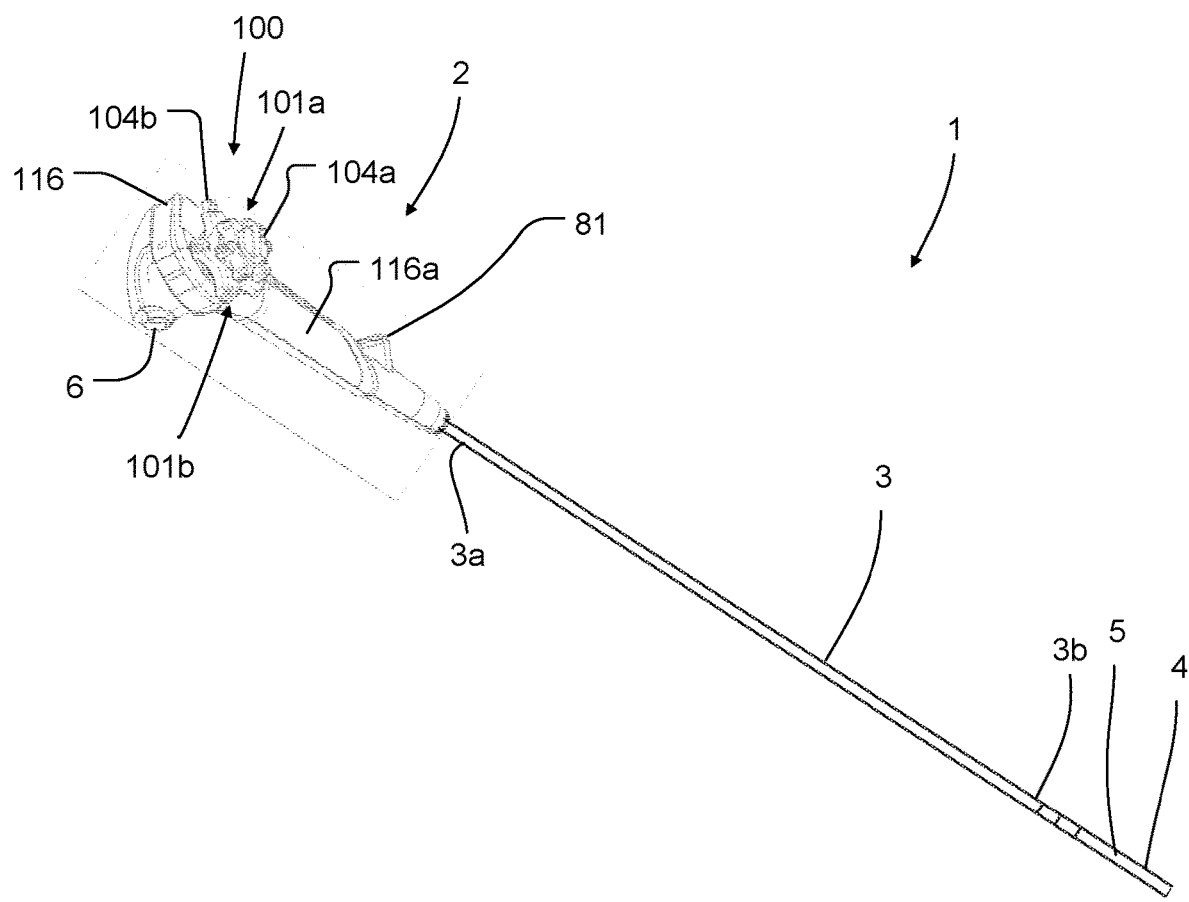
FIG. 1 shows a perspective view of an endoscope including a control system according to the present disclosure.
Figure 2:
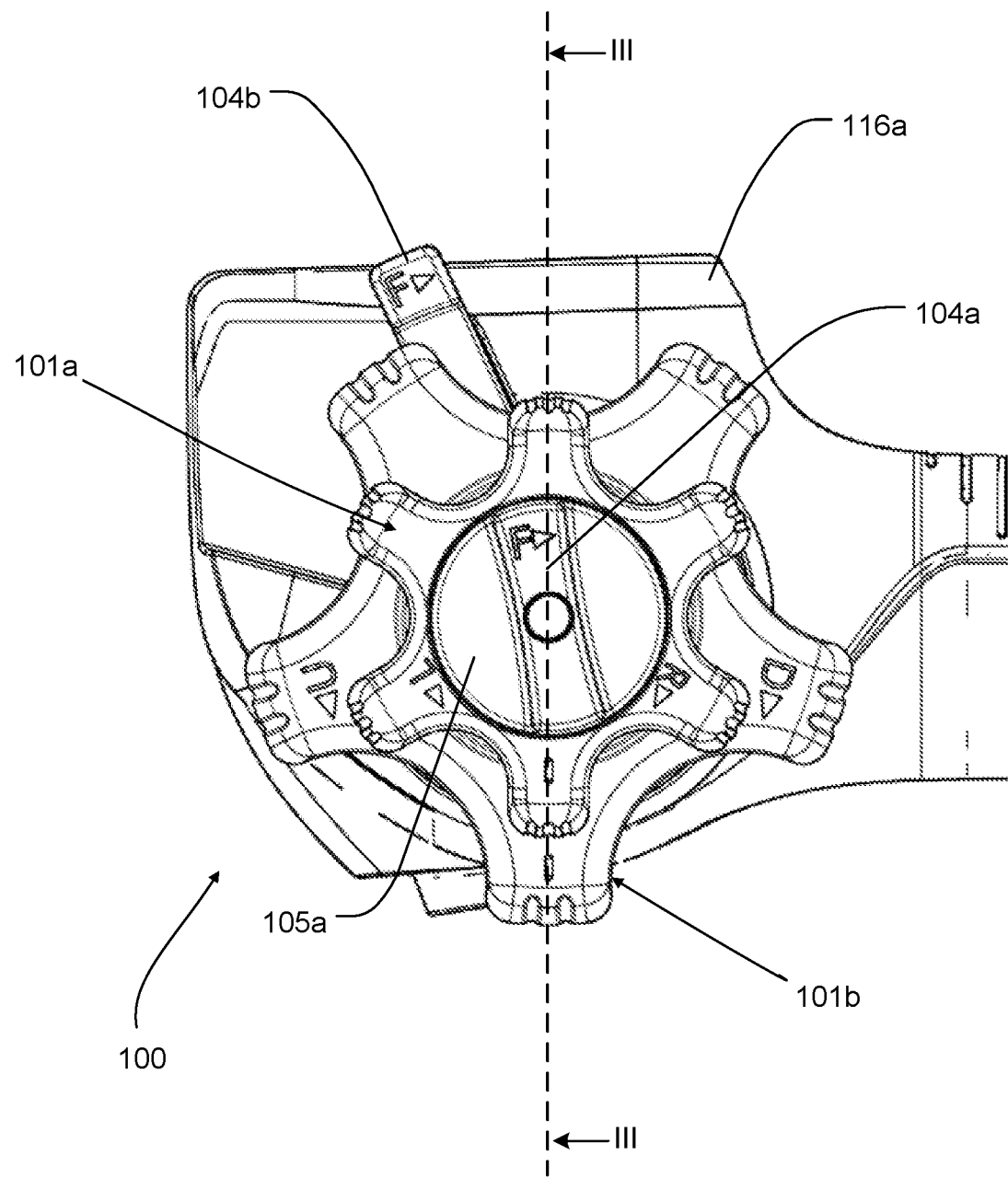
FIG. 2 shows a top view of the control system of FIG. 1.

FIG. 1 shows a disposable insertion endoscope 1 with a control system 100, an elongated insertion tube 3, and an endoscope handle 2 at a proximal end 3a of the elongated insertion tube 3. The endoscope handle includes a handle housing 116.

In a known manner, an endoscope tip 4 is positioned at a distal end 3b of the elongated insertion tube 3, the tip 4 comprising a bending section 5 positioned between the tip 4 and the elongated insertion tube 3. The endoscope handle 2 comprises the endoscope control system 100, the endoscope control system 100 being for performing a bending operation of the disposable insertion endoscope 1.

In a known manner, the bending section 5 is connected to steering wires, which extend from the control system 100 through the tube 3 to allow the control system 100 to activate a two-dimensional bending operation of the bending section 5 via the steering wires. The bending section 5 is configured to be articulated to maneuver the endoscope 1 inside a body cavity (not shown). The bending section 5 is bendable in two dimensions, i.e. an up/down dimension and a left/right dimension. In an alternative, not shown embodiment, the bending section is bendable in one dimension only.

The bending section 5 has increased flexibility achieved by articulated segments of the bending section 5 as is known in the art. The steering wires run along the inside of the elongated insertion tube 3 from the tip 4 through the bending section 5 to the endoscope control system 100. Still in a known manner, the maneuvering of the endoscope 1 inside the body can be carried out by tensioning or slacking the steering wires by means of the control system 100.

Still in a known manner, the distal tip 4 has a not shown built-in camera including a vision sensor. Not shown electrical wiring for the camera and potential other electronics, such as one or more LEDs accommodated in the tip part 4, run along the inside of the elongated insertion tube 3 from the endoscope handle 2 to a PCB or an FPC at or in the distal tip 4. A not shown suction/working channel runs along the inside of the insertion tube 3 from the handle 2 to the tip part 4, e.g. allowing liquid to be removed from the body cavity or allowing for insertion of a surgical instrument and/or a sampling instrument or other instruments (not shown) into the body cavity. The suction channel is connected to a suction connector 6 positioned at the proximal end of the handle 2. A sampling connector 81 is positioned at the distal end of the handle 2.

Figure 4:
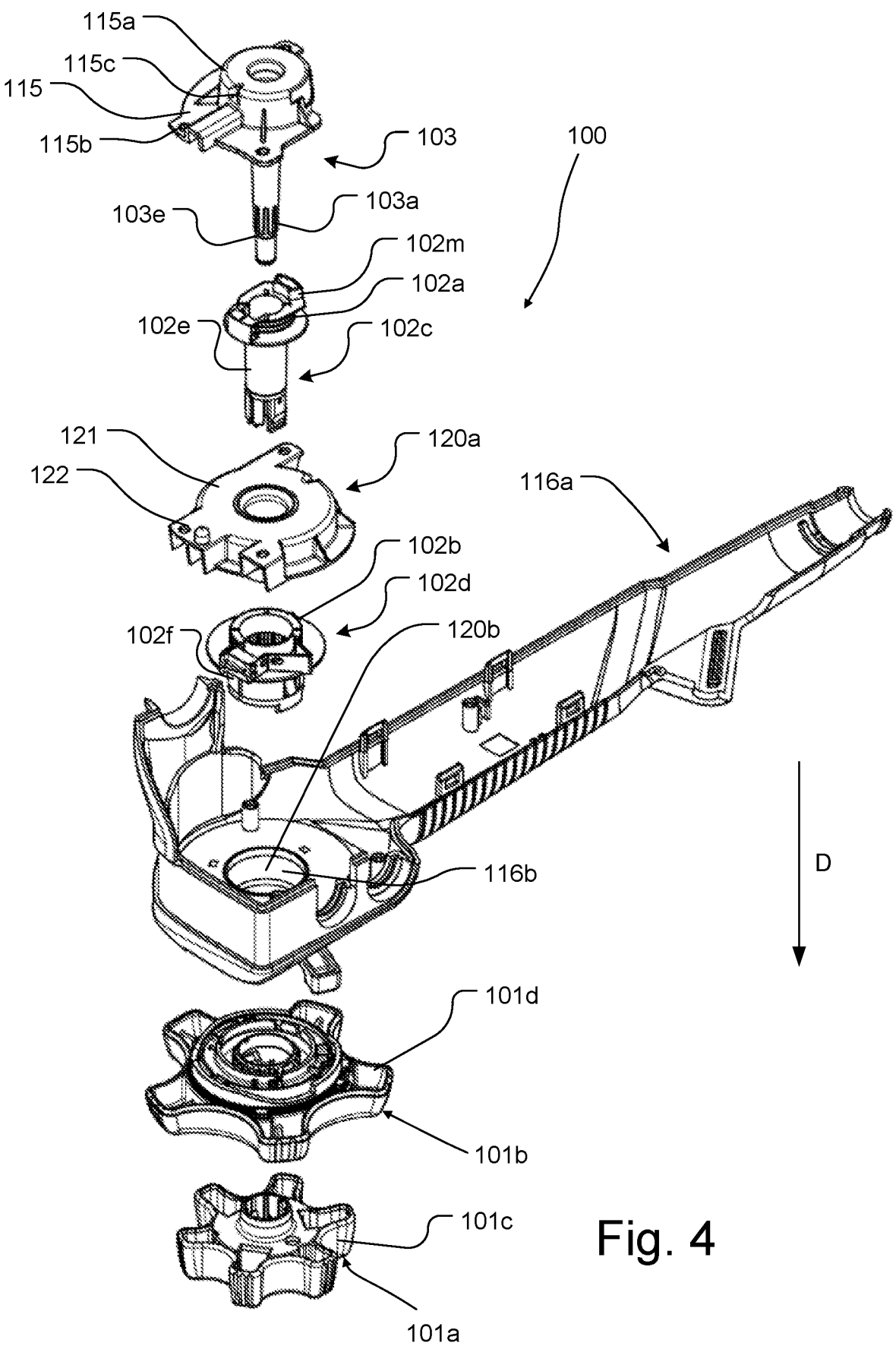
FIG. 4 shows an exploded perspective view of a handle frame and the control system of the endoscope of FIG. 1.

The endoscope control system 100 is shown exploded in FIG. 4 and comprises a housing frame 116a forming part of the handle housing 116 in the assembled endoscope 1, the housing frame 116a forming a half part of the assembled handle housing 116. The housing frame 116a at one end comprises a connection hole 116b.

The control system 100 further comprises a first control wheel unit 101a comprising a first wheel handle 101c comprising finger depressions and a second control wheel unit 101b comprising a second wheel handle 101d similarly comprising finger depressions.

The control system 100 further comprises a first shaft unit 102c and a second shaft unit 102d. The first shaft unit 102c comprises a first wire drum 102a and a first, sleeve-shaped shaft 102e, the first shaft 102e connecting the first control wheel unit 101a to the first wire drum 102a, the first wire drum 102a being for connection to a first steering wire 102k (shown in FIG. 7) of the endoscope 1, whereby rotation of the first wheel handle 101c relative to the housing frame 116a about an axis of rotation controls the bending operation in a first dimension. The second shaft unit 102d comprises a second wire drum 102b and a second shaft 102f, the second shaft 102f connecting the second control wheel unit 101b to the second wire drum 102b, the second wire drum 102b being for connection to a second steering wire 102l (shown in FIG. 10) of the endoscope 1, whereby rotation of the second wheel handle 101d relative to the housing frame 116a about an axis of rotation controls the bending operation in a second dimension. As described below, the first control wheel unit 101a and the first shaft unit 102c are coupled together in what may be referred to as a first control wheel 101 (best seen in FIG. 6), while the second control wheel unit 101b and the second shaft unit 102d are coupled together in what may be referred to as a second control wheel 102 (best seen in FIG. 10).

Referring to FIGS. 4 to 10, an embodiment of the methods of assembly of the control system 100 according to the present disclosure comprises, in sequence, the steps of:

1) holding the first control wheel unit 101a in a fixed position;
2) moving the second control wheel unit 101b in an assembly direction D to position the second control wheel unit 101b on the first control wheel unit 101a;
3) moving the housing frame 116a in the assembly direction D to position the housing frame 116a on the second control wheel unit 101b;
4) moving the second shaft unit 102d in the assembly direction D so that the second shaft is positioned to extend through the connection hole 116b of the housing frame 116a and snaps into engagement with the second control wheel unit 101b by means of a second snap connection 113 (shown in FIGS. 8-10) between the second shaft 102f and the second control wheel unit 101b; and
5) moving the first shaft unit 102c in the assembly direction D so that the first shaft 102e is positioned to extend through the connection hole 116b of the housing frame 116a and through the second shaft 102f and snaps into engagement with the first control wheel unit 101a by means of a first snap connection 112 (shown in FIGS. 5-7) between the first shaft 102e and the first control wheel unit 101a;

whereby the first and second control wheel units 101a, 101b, the housing frame 116a, and the first and second shaft units 102c, 102d are maintained in position relative to each other in the assembly direction D by means of the first and second snap connections 112, 113.

This method allows for mounting and positioning all the parts involved, i.e. the first and second control wheel units 101a, 101b, the housing frame 116a, and the first and second shaft units 102c, 102d from one side only and in the assembly direction D only. In each of the steps 2) to 5), only the next part to be added is moved in the assembly direction while the already assembled parts are not moved. Mounting and positioning all the parts involved from one side only simplifies assembly and such simplification and corresponding manufacturing cost reduction is made possible by the present embodiment. As described below, a jig could be used to assemble the parts in sequence. While the method may be performed with the steps 1) to 5) performed in sequence, the first and second control wheel units 101a, 102b could be mated before placing them onto the jig, and the first and second shaft units 102c, 102d could be assembled together before snapping the shafts onto the first and second control wheel units 101a, 102b. In another example, the first and second shaft units 102c, 102d and the housing frame 116a could be assembled together before snapping the shafts onto the first and second control wheel units 101a, 102b. In a further example, a jig could be used to assemble the system from the opposite direction, mounting the shafts on the jig and then, in the direction opposite D, snapping the first and second control wheel units 101a, 102b onto the first and second shaft units 102c, 102d. As can be deduced from the foregoing, the assembly advantages are derived from the structures of the components being assembled. The assembly direction D may be referred to as the axial direction.

The first control wheel unit, the second control wheel unit, the housing frame, the second shaft unit and the first shaft unit can be considered components of a stack, and the method can thus comprise stacking the components in order to form the stack. Stacking the components in order comprises holding a portion of the stack while moving the components onto the portion of the stack being held. The first control wheel unit can be considered part of the stack and can be held in the jig, as described, as the other components are stacked via movement in the axial direction toward the first control wheel unit. The stack may comprise an inner bearing element frame and a center shaft. The method may include, after moving the second shaft unit, moving the inner bearing element frame in the axial direction to position the inner bearing element frame through the connection hole of the housing frame. The inner bearing element frame has a portion positioned between the first shaft and the second shaft. The method may include, after moving the first shaft unit, moving a center shaft in the axial direction to position the center shaft through the first shaft and moving a cap in the axial direction toward the first control wheel unit to form a snap connection between a tip end of the center shaft and the cap to secure the center shaft in place.

Figure 11:
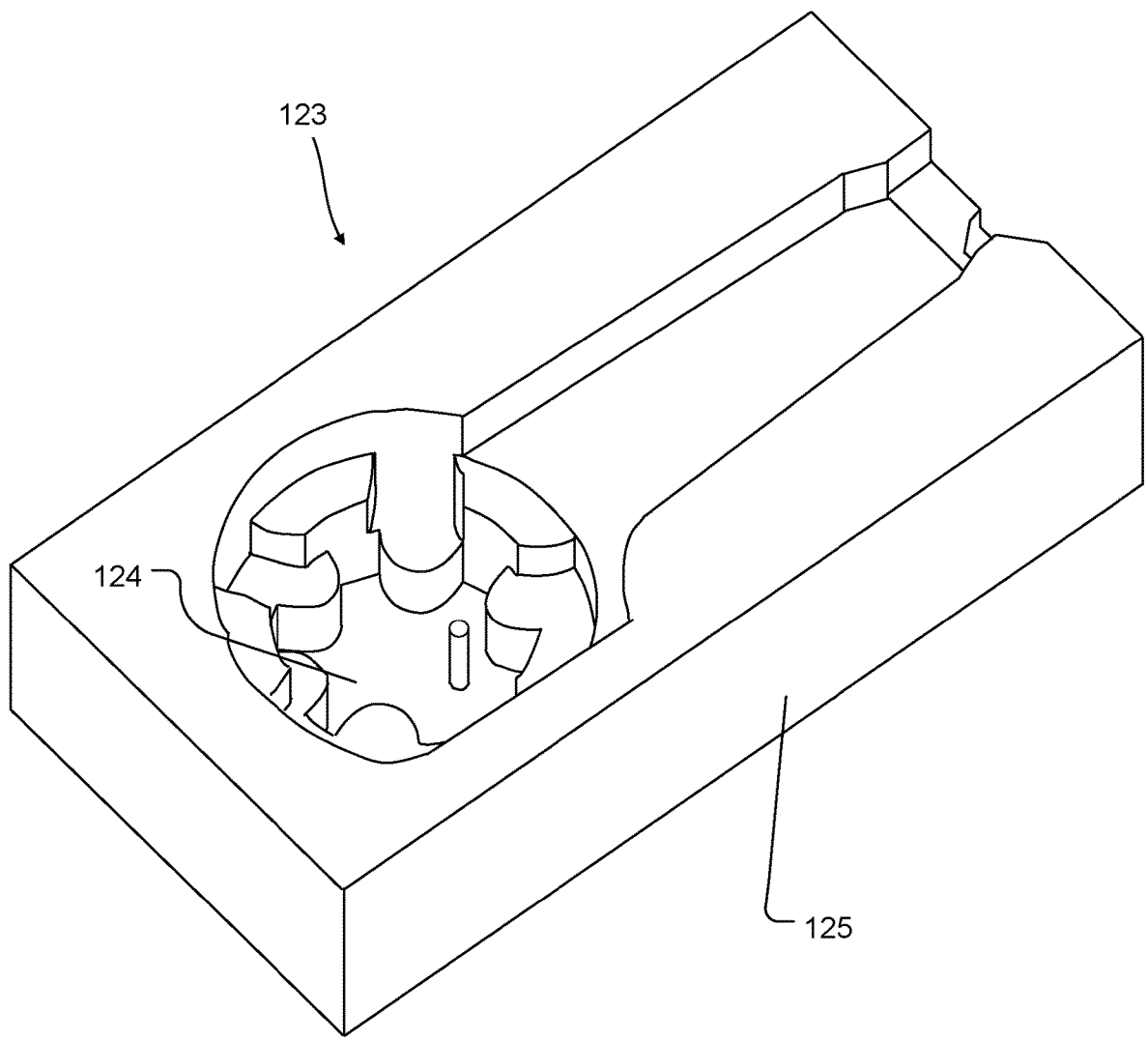
FIG. 11 shows a perspective view of a jig.

The first and second snap connections 112, 113 ensure that the parts of the control system assembled in steps 1) to 5) are attached to each other only by means of the movement carried out in steps 4) and 5). Accordingly, the movement in each of steps 4) and 5) activate the snap connections 112, 113 without any further action being required to activate these. No locking rings or separate locking elements are applied during or between steps 1) to 5). Flipping around or turning the already assembled parts is avoided during the sequence of steps 1) to 5). A jig 123 as shown in FIG. 11 is used as described below during the method steps 1) to 5), and the already assembled parts do not need to be removed from the jig 123 during steps 1) to 5).

The housing frame 116a is a first half shell of the handle housing 116a, the handle housing 116a further comprising a second half shell that is attached to the first half shell 116a after completion of steps 1) to 5). Hereby, the first and second wire drums 102a, 102b are positioned inside the assembled handle housing 116.

The first and second wheel handles 101c, 101d are generally circular and/or comprise conventionally provided finger depressions or cut-outs.

Figure 8:
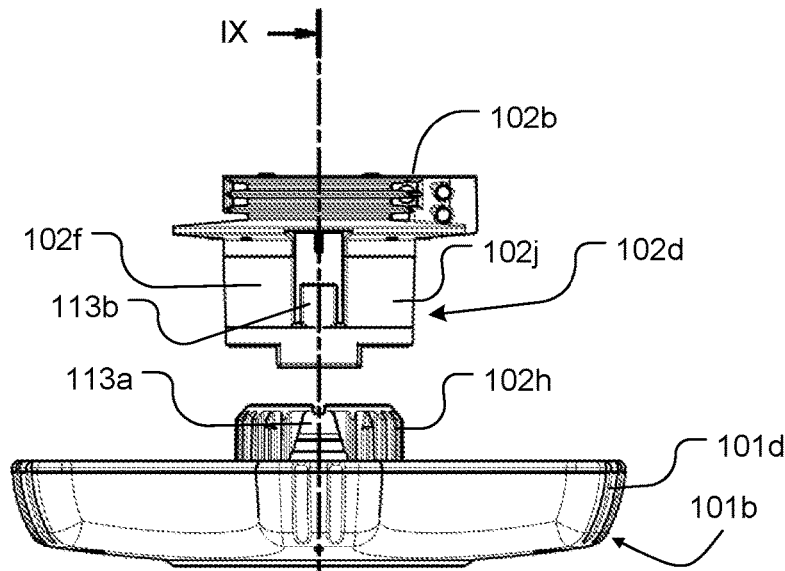
FIG. 8 shows an exploded side view of a second control wheel unit and a second shaft unit of the control system of FIG. 1.
Figure 9:
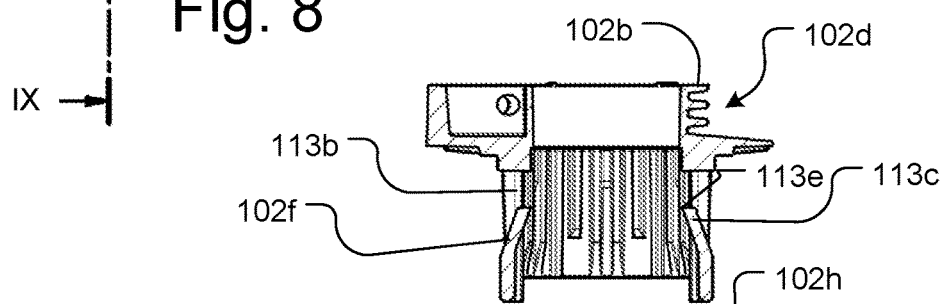
FIG. 9 shows a cross-sectional view taken along the line IX-IX of FIG. 8.
Figure 10:
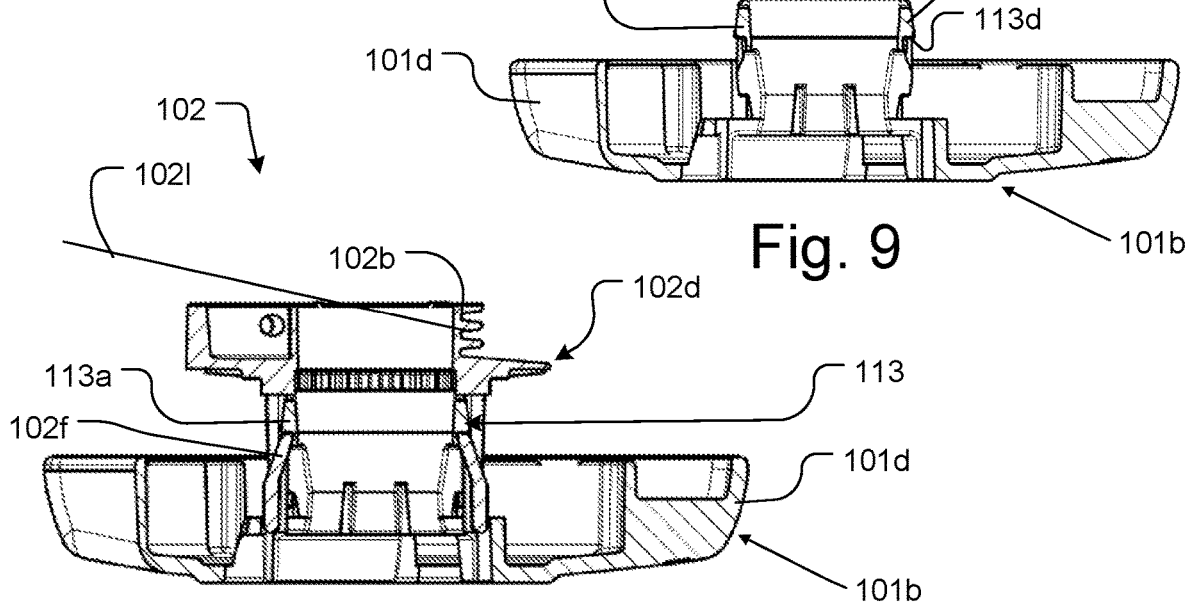
FIG. 10 shows a view like that of FIG. 9, wherein the second control wheel unit and second shaft unit are in an assembled state.

FIGS. 5-7 describe the components of and the first snap connection 112, and FIGS. 8-10 describe the components of and the second snap connection 113. Each of the first and second control wheel units 101a, 101b comprises a central part or wheel sleeve 102g, 102h, first and second, respectively, each surrounding a center opening. The central parts 102g, 102h are cylindrical and extend towards the housing frame 106a in the assembled control system 100. In the assembled control system 100, the second central part 102h may in other embodiments extend to encompass part of the first central part 102g in the assembled state of the control system 100.

The first shaft 102e comprises a bearing surface 102i, and the second shaft 102f comprises a bearing surface 102j, the bearing surfaces 102i, 102j being for abutment and rotational sliding on associated bearing elements fixed to the housing frame 116a, see further below.

The first and second shafts 102e, 102f are each tubular and each comprises a substantially cylindrical circumferential wall which provide the associated bearing surfaces 102i, 102j. A diameter of the first shaft 102e is smaller than that of the second shaft 102f.

The axes of rotation of the control wheel units 101a, 101b are coinciding to form one axis of rotation, which is also a center axis of the control system 100. This axis extends in the assembly direction D. The first and second shafts 102e, 102f, the first and second control wheel units 101a, 101b, and the first and second wheel handles 101c, 101d extend coaxially in the assembled control system 100.

In the assembled control system 100, as shown in FIG. 4, the first and second wire drums 102a, 102b on the one hand and the first and second wheel handles 101c, 101d on the other hand are positioned on opposite sides of the connection hole 116b of the housing frame 116a. The first wire drum 102a is positioned in extension of the second wire drum 102b and farther from the housing frame 116a or the connection hole 116b than the second wire drum 102b.

The first and second wire drums 102a, 102b are positioned at upper ends of the first and second shafts 102e, 102f, respectively.

The assembled control system 100 further includes an inner bearing element 120a which in a further step after step 4) is moved in the assembly direction D to extend through the second shaft unit 102d and through the connection hole 116b of the housing frame 116a. In the assembled control system 100, the inner bearing element 120a is rotationally fixed to the housing frame 116a. The inner bearing element 120a comprises an inner bearing surface 120c (FIG. 3) positioned farther from the common axis of rotation than the outer bearing surface 102i of the first shaft 102e, the inner bearing surface 120c abutting the outer bearing surface 102i so that rotation of the second control wheel unit 101b is at least partly borne on the inner bearing element 120a. The inner bearing element 120a includes a cylindrical, tubular inner bearing sleeve having a wall. The inner bearing element 120a separates rotation of the control wheel units 101a, 101b from each other.

The assembled control system further comprises an outer bearing element 120b in one piece with the housing frame 116a. The outer bearing element 120b surrounds and defines the connection hole 116b of the housing frame 116a. The outer bearing element 120b is tubular and cylindrical and comprises a wall which extends away from the housing frame 116a in a direction towards the first control wheel unit 101a. The outer bearing element 120b comprises an inner bearing surface 120d (FIG. 3) positioned farther from the common axis of rotation than the outer bearing surface 102j of the second shaft 102f, the inner bearing surface 102j abutting the outer bearing surface 102j so that rotation of the second control wheel unit 101b is at least partly borne on the outer bearing element 120b. The outer bearing element 120b is an outer bearing sleeve that encompasses at least part of the second shaft 102e.

The control system 100 further includes a center shaft 103 which, in a further step after step 5), is moved in the assembly direction D to extend through the connection hole 116b of the housing frame 116a, the first and second shaft units 102c, 102d, and the center openings of the first and second control wheel units 101a, 101b. The center shaft 103 comprises a connector frame or center shaft frame 115, and the connector frame 115 is fixed by means of pins (not shown) to the housing frame 116a via the inner bearing element frame 121, see below, after insertion of the center shaft 103 so that the center shaft 103 is fixed to the housing frame 116a (not shown). The connector frame 115 extends radially from a shaft part 103a of the center shaft 103 and is positioned within the handle housing 116a in the assembled endoscope 1, see FIG. 3. The connector frame 115 includes a housing 115a including a flange 115b fixed to the housing frame. The housing 115a includes an indentation 115c that operates as stop or stop surface when it contacts a corresponding stop surface 102m on a longitudinally protruding portion of the first shaft unit 102c as it rotates. The protruding portion has an arcuate shape and its length determines the angle of rotation of the first shaft unit 102c.

Similarly, the inner bearing element 120a includes an inner bearing element frame 121 that extends radially from a sleeve part 120e thereof and is positioned within the handle housing 116 in the assembled endoscope 1. The inner bearing element frame 121 is directly fixed to the housing frame 116a, the center shaft frame 115 being directly fixed to the inner bearing element frame 121 by means of screws (not shown) so as to be indirectly fixed to the housing frame 116a. The screws are inserted into screw holes, one of these being designated 122 in FIG. 4.

When the center shaft 103 has been positioned, a cap 105a is moved opposite to the assembly direction D to be attached to a tip end 103b of the center shaft 103 by a snap connection 103c which is provided in a manner similar to the first and second snap connections 112, 113. Accordingly, the cap 105a includes two resilient and pushable connection parts 103d, whereas the tip end 103b includes associated two connection parts taking the form of recesses 103e. This snap engagement 103c is similarly be activated during or at the end of the insertion of the center shaft 103 into the control system 100. The cap 105a covers and attaches a first multi-disc brake 110a of the first control wheel unit 101a, see further below. The brake 110a is encased within a spacing defined by interior surfaces of the first wheel handle 101c. Before insertion of the brake 110a and subsequent positioning of the cap 105a, i.e. after steps 1) to 5), the assembled parts of the control system 100 are removed from the jig 123 and the assembled parts of the control system 100 are flipped around, i.e. turned 180 degrees, after which the first brake 110a is assembled and positioned to form part of the first control wheel unit 101a, after which, again, the cap 105a is positioned as described. Alternatively, the brake 110a and the cap 105a are mounted to form part of the first control wheel unit 101a before or during step 1). The cap 105a includes a brake knob 104a projecting in the assembly direction and upon rotation of which the brake 110a is activated to brake rotation of the first control wheel unit 101a and, thus, first shaft unit 102d.

In the assembled control system 100, a brake handle 104b for activation of a similar, second multi-disc brake 110b, which brakes the second control wheel unit 101b in a similar manner, is attached to the housing frame 116a. During the method of assembly, when the second control wheel unit 101b has been positioned in step 2), before step 3), the brake handle 104b is moved in the assembly direction to be positioned on the second control wheel unit 101b.

In step 1), the first control wheel unit is positioned in and at the bottom of a correspondingly shaped part of a jig depression 124 of the jig 123 shown in FIG. 11, the jig 123 holding the first control wheel unit 101a in a fixed position. In step 2), the second control wheel unit is also positioned and held in a correspondingly shaped part of the jig depression 124. In step 3), the housing frame is also positioned and held in a correspondingly shaped part of the jig depression 124. The jig 123 includes a jig block 125 with in which the jig depression 123 is shaped to provide a positive engagement with the first control wheel unit 101a, especially the first wheel handle 101c. Similarly, the jig depression 124 is shaped to also provide a positive engagement with the second control wheel unit 101b, especially the second wheel handle 101d, when the second control wheel unit 101b is positioned on the first control wheel unit 101a in the jig 123. Similarly, the jig depression 124 is shaped to also provide a positive engagement with the housing frame 116a when the housing frame 116a is positioned on the second control wheel unit 101b in the jig 123. Hereby, all of these elements can be maintained in relative positions until the snap connections 112, 113 are engaged in steps 4) and 5).

After steps 1) to 5), the assembled control system 100 is removed from the jig 123, and further assembly occur as described. This involves assembly of the handle housing 116.

Referring to FIGS. 8 to 10, the second snap connection 113 axially and rotationally fixes the second shaft unit 102d to the second control wheel unit 101b. The second snap connection 103 includes two connection parts 113a in the form of resilient projections or pins of the second control wheel unit 101b which interlock with two associated connection parts 113b, embodied by recesses, of the second shaft unit 102d. These connection parts 113a, 113b are thus mutually engaging. During the movement of the second shaft unit 102d, the connection parts 113a are pushed in a radial direction (inwardly) and, then, when the second shaft unit 102d is further moved or inserted, resiliently snap back to engage with the associated connection parts 113b. The connection parts 113b includes a ramp or inclined surface 113c, which forces the pushable connection parts 113a inwardly in a radial direction during the movement of the second shaft unit 102d. Accordingly, the pushable connection parts 113a include a barb surface 113d which during the snap moves into engagement with an associated barb surface 113e of the other connection parts 113b to secure the position of the second shaft unit 102d to the second control wheel unit 101b. The pushable connection parts 113a are included in the second central part 102h, and the associated connection parts 113b are included in the second shaft unit 102d. The pushable connection parts 103a may each be provided by two axially extending slots defining a resilient, axially moveable pin between them, as in conventional snap fittings.

As described, the second snap connection 113 includes a barb surface 113d which during the snap moves into engagement with an associated barb surface 113e to secure the position of the second shaft unit 102d relative to the second control wheel unit 101b. As shown, opposed walls, each comprising an inwardly projecting angled portion extending from a vertical portion below it, are provided on the second shaft unit 102d. Each of the inwardly projecting angled portions includes an inclined surface 113c and ends a the barb surface 113e. In alternative embodiments, the inwardly projecting angled portion can be resilient and the connection parts 113a can be of various rigidities, since the inwardly projecting angled portions can flex outwardly to allow the two connection parts 113a to move past them into the cavities 113b. Thus, the second snap connection 113 is made by opposing barb surfaces, at least one of which is provided by a radially resilient part.

Referring to FIGS. 5 to 7, like the second snap connection 113, the first snap connection 112 axially and rotationally fixes the first shaft unit 102c to the first control wheel unit 101a. And the first snap connection 112 includes two connection parts 112a of the first shaft unit 102c interlocking with two associated connection parts 112b (best seen in FIG. 7) of the first control wheel unit 101a. These associated connection parts 112a, 112b mutually engage. During the movement of the first shaft unit 102c, the connection parts 112a are pushed inwardly in the radial direction by the wheel sleeve 102g and, then, when the first shaft unit 102c is further moved and inserted, resiliently snap back to engage the associated connection part 112b. And again, this is achieved by the connection parts 112b including a ramp or inclined surface 112c, which forces the pushable connection parts 112a in the radial direction during the movement of the first shaft unit 102c. Accordingly, the pushable connection parts 112a include a barb surface 112d which during the snap moves into engagement with an associated, opposed barb surface 112e of the connection parts 112b to secure the position of the first shaft unit 102c to the first control wheel unit 101a. The pushable connection parts 112a are included in the first shaft unit 102c, in the first shaft 102e thereof, and the associated connection parts 112b are included in the first control wheel unit 101a. The pushable connection parts 112a may be provided by two axially extending slots defining a resilient, axially moveable pin between them.

As described, the first snap connection 112 includes a barb surface 112d which during the snap moves into engagement with an associated barb surface 112e to secure the position of the first unit 102c relative to the second control wheel unit 101a. In alternative embodiments, the connection parts 112b do not need to include a ramp or inclined surface 112c. The pushable connection parts 112a each includes a ramp or inclined surface at the distal end thereof, which can force the pushable connection parts 112a inwardly in the radial direction during the movement of the first shaft unit 102c when the ramps contact the inner surface of the wheel sleeve 102g. Thus, the first snap connection 112 is made by opposing barb surfaces, at least one of which is provided by a radially resilient part.

Hereby, the first and second snap connections 112, 113, when engaged, prevent movement of the first and second control wheels 101a, 101b, the housing frame 116a, and the first and second shaft units 102c, 102d relative to each other in the assembly direction D. Accordingly, the barb surfaces 112d, 112e; 113d, 113e face in the axial direction and are mutually opposed to each other during and after assembly. Barbs of the connection parts 112a, 113a are provided as projections extending in the radial direction.

The assembly direction D is parallel with the axes of rotation of the first and second control wheel units 101a, 101b.

Figure 3:
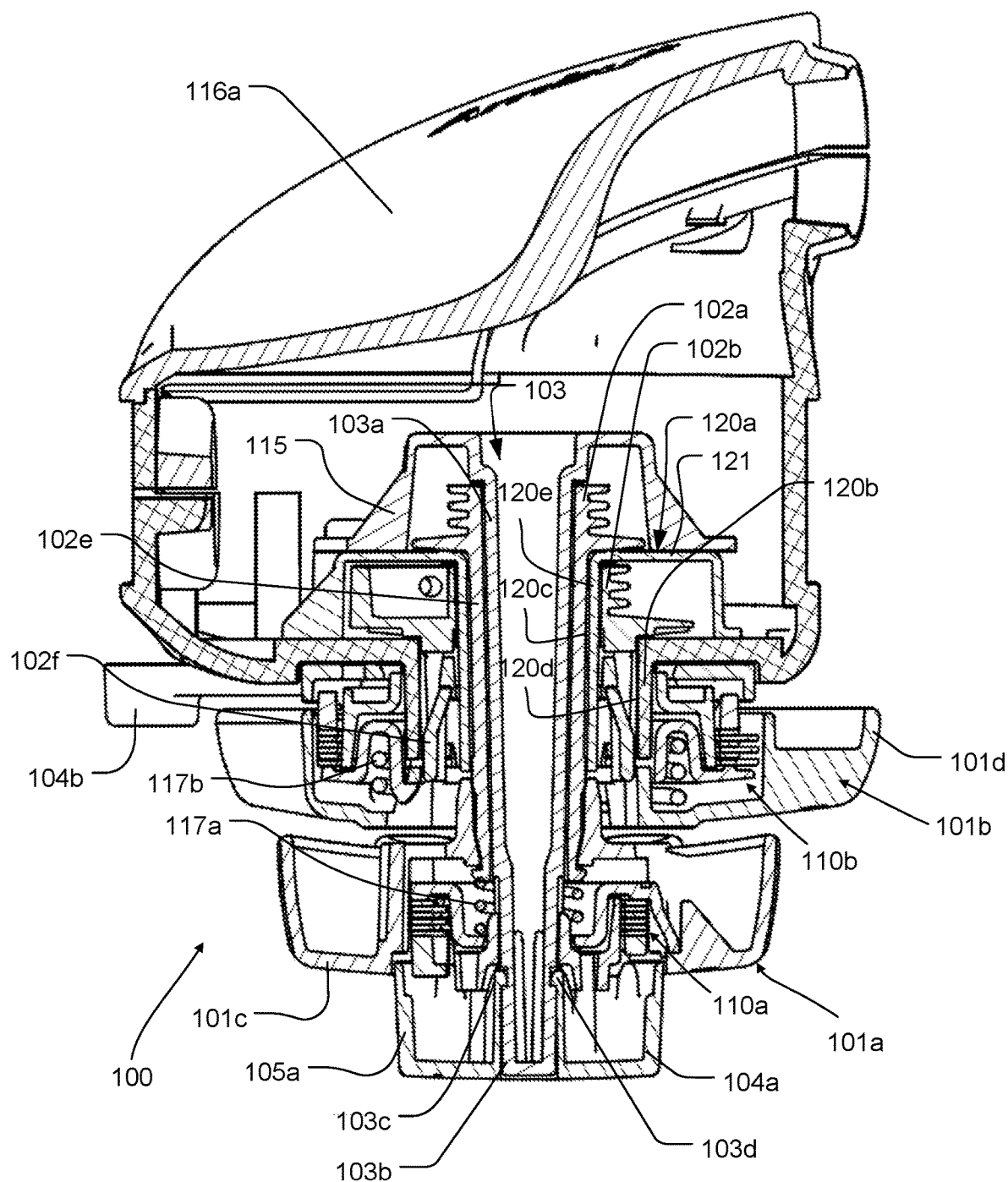
FIG. 3 shows a cross-sectional view taken along line III-III in FIG. 2.

As shown in FIG. 3, in the assembled control system 100, the first and second control wheel units 101a, 101b house the associated brakes 110a, 110b. Activation of each of the brakes 110a, 110b moves the brake from a released position to a braking position. A brake force of the brake 110a, 110b in the braking position brakes rotation of the associated control wheel unit 101a, 101b, respectively. The brake force is released in the released position. The brake 110b is assembled in the second wheel handle before step 1). The brakes 110a, 110b each includes a stack of brake discs and a helical spring 117a, 117b, respectively.

After assembly of the control system 100 and then the handle 2, the control system 100 forms part of the handle 2.

Rotation of the control wheel units 101a, 10b occurs relative to the housing frame 116a during the bending operation.

The handle housing 116 takes the form of a housing shell.

The first and/or second wire drums 102a, 102b are pulleys. In the assembled endoscope 1, the first and second steering wires are attached to the wire drums 102a, 102b to be woundable on these, respectively.

Any one or more of or all steps 1) to 5) can be carried out manually and/or automatically. Any one or more or all of the further steps of assembly may also be carried out manually and/or automatically.

In each of steps 2) to 5), all already positioned parts of the control system 100 remain in the held position.

The snap connection parts 112a, 112b; 113b, 113a are provided in one piece with the first shaft unit 102c and the first control wheel unit 101a; the second shaft unit 102d and the second control wheel unit 101b, respectively.

The foregoing aspects are further embodied in the following exemplary items:

Item 1. A method of assembly of an endoscope control system, the endoscope control system being for performing a bending operation in a disposable insertion endoscope, wherein the endoscope control system comprises: a housing frame for forming or for forming part of an endoscope handle housing, the housing frame comprising a connection hole; a first control wheel unit comprising a first wheel handle; a second control wheel unit comprising a second wheel handle; a first shaft unit, the first shaft unit comprising a first wire drum and a first shaft, the first shaft connecting the first control wheel unit to the first wire drum, the first wire drum being for connection to a first steering wire of the endoscope, whereby rotation of the first wheel handle relative to the housing frame about an axis of rotation controls the bending operation in a first dimension; a second shaft unit, the second shaft unit comprising a second wire drum and a second shaft, the second shaft connecting the second control wheel unit to the second wire drum, the second wire drum being for connection to a second steering wire of the endoscope, whereby rotation of the second wheel handle relative to the housing frame about an axis of rotation controls the bending operation in a second dimension; and
  wherein the method of assembly comprises, in sequence, the steps of:
  1) holding the first control wheel unit in a position;
  2) moving the second control wheel unit in an assembly direction to position the second control wheel unit on the first control wheel unit;
  3) moving the housing frame in the assembly direction to position the housing frame on the second control wheel unit;
  4) moving the second shaft unit in the assembly direction so that the second shaft is positioned to extend through the connection hole of the housing frame and snaps into engagement with the second control wheel unit by means of a second snap connection between the second shaft and the second control wheel unit; and 5) moving the first shaft unit in the assembly direction so that the first shaft is positioned to extend through the connection hole of the housing frame and through the second shaft and snaps into engagement with the first control wheel unit by means of a first snap connection between the first shaft and the first control wheel unit;

whereby the first and second control wheel units, the housing frame, and the first and second shaft units are maintained in position relative to each other in the assembly direction by means of the first and second snap connections.

Item 2. The method of item 1, wherein all the movements of steps 2) to 5) are carried out from one side only.

Item 3. The method of item 1 or 2, wherein, in each of steps 2) to 5), all already positioned parts of the control system to be assembled remain in a held position.

Item 4. The method of any one of the previous items, wherein only the movement carried out in steps 4) and 5) affect the attachment of the parts assembled in steps 1) to 5) to each other.

Item 5. The method of any one of the previous items, wherein, during the sequence of steps 1) to 5), no separate locking device is applied to attach the parts to each other.

Item 6. The method of any one of the previous items, wherein the first and second snap connections are provided only by snap connection parts provided in one piece with the first shaft unit, the first control wheel unit, the second shaft unit, and the second control wheel unit, respectively.

Item 7. The method of any one of the previous items, wherein the first snap connection comprises at least one primary connector part forming part of the first shaft unit and at least one secondary connector part forming part of the first control wheel unit, the primary and secondary connector parts in step 5) snapping directly onto each other to form the first snap connection; and wherein the second snap connection comprises at least one tertiary connector part forming part of the second shaft unit and at least one quaternary connector part forming part of the second control wheel unit, the tertiary and quaternary connector parts in step 4) snapping directly onto each other to form the second snap connection.

Item 8. The method of any one of the previous items, wherein no further steps are involved in the method during the sequence of steps 1) to 5).

Item 9. The method of any one of the previous items wherein, before step 1), the first wheel is positioned in a jig, the first wheel being held in the jig in step 1) and during the sequence of steps 2) to 5).

Item 10. An endoscope control system for performing a bending operation in a disposable insertion endoscope, wherein the endoscope control system comprises:
 a housing frame for forming or for forming part of an endoscope handle housing, the housing frame comprising a connection hole;
 a first control wheel unit comprising a first wheel handle;
 a second control wheel unit comprising a second wheel handle;
 a second shaft unit, the second shaft unit comprising a second wire drum and a second shaft, the second shaft connecting the second control wheel unit to the second wire drum, the second wire drum being for connection to a second steering wire of the endoscope, whereby rotation of the second wheel handle relative to the housing frame about an axis of rotation controls the bending operation in a second dimension;
 wherein the second control wheel is positioned between the first control wheel and the housing frame, the second shaft extends through the connection hole of the housing frame, and the first shaft extends through the connection hole of the housing frame and through the second shaft; and
 wherein the first shaft is connected to the first control wheel unit by means of a first snap connection between the first shaft and the first control wheel unit, and the second shaft is connected to the second control wheel unit by a second snap connection between the second shaft and the second control wheel unit,
 whereby the first and second snap connections attach the first and second control wheels, the housing frame, and the first and second shaft units to each other.

Item 11. The control system according to item 10, wherein the first and second snap connections maintain attachment between the first and second control wheels, the housing frame, and the first and second shaft units if all other parts are removed.

Item 12. The control system according to item 10 or 11, wherein the first and second snap connections are provided by snap connection parts provided in one piece with the first shaft unit, the first control wheel unit, the second shaft unit, and the second control wheel unit, respectively.

Item 13. The endoscope control system according to any one of items 10 to 12, wherein the endoscope control system has been assembled according to the method of any one of items 1 to 9.

Item 14. An endoscope comprising the control system assembled according to any one of items 1 to 9 and/or comprising the control system according to any one of items 10 to 13.

Item 15. The endoscope according to item 14, further comprising the first and second steering wires and a distal tip or tip part that comprises a bending section connected to the first and second steering wires so that the control system can activate the bending operation of the bending section via the steering wires.

Item 16. The endoscope according to item 14, wherein the first shaft includes a bearing surface, the second shaft includes an outer bearing surface positioned farther from the axis of rotation than the bearing surface of the first shaft, and the handle housing includes an outer bearing element comprising an inner bearing surface positioned farther from the axis of rotation than the outer bearing surface of the second shaft, the inner bearing surface of the outer bearing element abutting the outer bearing surface of the second shaft so that rotation of the second control wheel is at least partly borne on the outer bearing element.

Item 17. The endoscope of item 16, further comprising an inner bearing element framed disposed at least in part between the first shaft and the second shaft, wherein the inner bearing element frame axially separates the first and second control wheel units from each other.

LIST OF REFERENCE SIGNS

1 Endoscope
2 Endoscope handle
3 Elongated insertion tube
3a Proximal end of insertion tube 3
3b Distal end of insertion tube 3
4 Tip
5 Bending section 6 Suction connector
7 Working channel port
100 Endoscope control system
101 First control wheel
101a First control wheel unit
101b Second control wheel unit
101c First wheel handle
101d Second wheel handle
102 Second control wheel
102a First wire drum
102b Second wire drum
102c First shaft unit
102d Second shaft unit
102e First shaft
102f Second shaft
102g First central part
102h Second central part
102i Bearing surface of the first shaft
102j Bearing surface of the second shaft
102k First steering wire
102l Second steering wire
103 Center shaft
103a Shaft part
103b Tip end
103c Snap connection
103d Connection parts
103e Recesses
104a Brake knob
104b Brake handle
105a Cap
110a First multi-disc brake
110b Second multi-disc brake
111 Stack of brake discs
112 First snap connection
112a Snap connection parts
112b Snap connection parts
112c Ramps
112d Barb surface
112e Barb surface
113 Second snap connection
113a Snap connection parts
113b Snap connection parts
113c Ramps
113d Barb surface
113e Barb surface
115 Connector/center shaft frame
116 Handle housing
116a Housing frame
116b Connection hole
117a Spring
117b Spring
120a Inner bearing element
120b Outer bearing element
120c Inner bearing surface
120d Inner bearing surface
120e Sleeve part
121 Inner bearing element frame
122 Screw hole
123 Jig
124 Jig depression
125 Jig block
D Assembly direction

I claim:

1. An endoscope comprising:
a handle comprising a housing frame and an outer bearing sleeve, the housing frame defining an interior of the handle and formed in one piece with the outer bearing sleeve, the outer bearing sleeve extending outwardly from the interior of the housing and including an inner bearing surface and a connection hole;
a bending section; and
a control system including:
an inner bearing element sleeve;
a first control wheel unit comprising a first wheel handle;
a second control wheel unit comprising a second wheel handle;
a first shaft unit comprising a first shaft connected to the first control wheel unit by a first snap connection; and
a second shaft unit comprising a second shaft having a central hole sized and shaped to receive therethrough the first shaft and defining an axial direction, the second shaft connected to the second control wheel unit by a second snap connection, the second shaft having an outer bearing surface bearing on the inner bearing surface of the outer bearing sleeve of the housing;
wherein the second control wheel is positioned between the first control wheel and the housing frame, the second shaft extends through the connection hole of the housing frame, and the first shaft extends through the connection hole of the housing frame and through the second shaft,
wherein the first and second snap connections attach the first and second control wheel units, the housing frame, and the first and second shaft units to each other, and
wherein the second snap connection is positioned intermediate the inner bearing element sleeve and the outer bearing sleeve.

2. The endoscope of claim 1, wherein the first snap connection comprises at least one primary connector part forming part of the first shaft unit and at least one secondary connector part forming part of the first control wheel unit, the primary and secondary connector parts snapping directly onto each other to form the first snap connection; and wherein the second snap connection comprises at least one tertiary connector part forming part of the second shaft unit and at least one quaternary connector part forming part of the second control wheel unit, the tertiary and quaternary connector parts snapping directly onto each other to form the second snap connection.

3. The endoscope of claim 1, wherein the first and second snap connections maintain attachment between the first and second control wheels, the housing frame, and the first and second shaft units even if the first and second control wheels, the housing frame, and the first and second shaft units are removed from the endoscope while still snap-attached.

4. The endoscope of claim 1, wherein the first and second snap connections are provided by snap connection parts provided in one piece with the first shaft unit, the first control wheel unit, the second shaft unit, and the second control wheel unit, respectively.

5. The endoscope of claim 1, further comprising an inner bearing element having a portion thereof positioned between the first shaft and the second shaft, a center shaft having a portion thereof positioned within the second shaft, and a cap forming a third snap connection with a tip end of the center shaft.

6. The endoscope of claim 1, further comprising a first steering wire, a second steering wire, and a distal tip or tip part that comprises the bending section, wherein the first shaft unit comprises a first wire drum operable to spool the first steering wire upon the rotation of the first wheel handle and the second shaft unit comprises a second wire drum operable to spool the second steering wire upon the rotation of the first wheel handle.

7. A method of assembly of the endoscope of claim 1, the method comprising:
    moving the second control wheel unit in the axial direction to position the second control wheel unit on the first control wheel unit;
    moving the housing frame of the handle of the endoscope in the axial direction to position the housing frame on the second control wheel unit;
    moving the second shaft unit in the axial direction to position the second shaft through the connection hole of the housing frame until the second shaft snaps into engagement with the second control wheel unit forming the second snap connection; and
    moving the first shaft unit in the axial direction to position the first shaft through the central hole of the second shaft and through the connection hole until the first shaft snaps into engagement with the first control wheel unit forming the first snap connection.

8. The method of claim 7, wherein moving the second control wheel unit, the housing frame, the second shaft unit and the first shaft unit comprise moving the second control wheel unit, the housing frame, the second shaft unit and the first shaft unit toward the first control wheel unit.

9. The method of claim 8, wherein the first control wheel unit, the second control wheel unit, the housing frame, the second shaft unit and the first shaft unit are components of a stack, and wherein the method comprises stacking the components in order to form the stack.

10. The method of claim 9, wherein stacking the components in order further comprises holding a portion of the stack while moving the components onto the portion of the stack being held.

11. The method of claim 10, wherein the method further comprises holding the first wheel handle in a jig, and then stacking the components onto the first control wheel unit.

12. The method of claim 9, wherein the method further comprises, after moving the second shaft unit, moving the inner bearing element sleeve in the axial direction to position the inner bearing element sleeve through the connection hole of the housing frame.

13. The method of claim 12, wherein the method further comprises, after moving the first shaft unit, moving a center shaft in the axial direction to position the center shaft through the first shaft and moving a cap in the axial direction toward the first control wheel unit to form a snap connection between a tip end of the center shaft and the cap to secure the center shaft in place.

14. The method of claim 7, wherein moving the second control wheel unit, the housing frame, the second shaft unit and the first shaft unit are carried out from one side only.

15. The method of claim 14, wherein the second control wheel unit, the housing frame, the second shaft unit and the first shaft unit remain in a held position after each has been positioned.

16. The method of claim 7, wherein forming the first snap connection and the second snap connection are sufficient to attach the first control wheel unit, the second control wheel unit, the housing frame, the second shaft unit and the first shaft unit to each other.

17. The method of claim 16, wherein, during the moving of the second control wheel unit, the housing frame, the second shaft unit and the first shaft unit, no separate locking device is applied to attach the first control wheel unit, the second control wheel unit, the housing frame, the second shaft unit and the first shaft unit to each other.

18. The method of claim 7, wherein the first and second snap connections are provided only by snap connection parts provided in one piece with each of the first shaft unit, the first control wheel unit, the second shaft unit, and the second control wheel unit, respectively.

19. An endoscope comprising:
    a handle comprising a housing frame and an outer bearing sleeve, the housing frame defining an interior of the housing and formed in one piece with the outer bearing sleeve, the outer bearing sleeve extending outwardly from the interior of the housing and including an inner bearing surface and a connection hole;
    a bending section; and
    a control system including:
    a first control wheel unit comprising a first wheel handle;
    a second control wheel unit comprising a second wheel handle;
    a first shaft unit comprising a first shaft connected to the first control wheel unit by a first snap connection;
    a second shaft unit comprising a second shaft having a central hole sized and shaped to receive therethrough the first shaft and defining an axial direction, the second shaft connected to the second control wheel unit by a second snap connection, the second shaft having an outer bearing surface bearing on the inner bearing surface of the outer bearing sleeve of the housing;
    an inner bearing element sleeve positioned between the first shaft and the second shaft,
    wherein the second control wheel is positioned between the first control wheel and the housing frame, the second shaft extends through the connection hole of the housing frame, and the first shaft extends through the connection hole of the housing frame and through the second shaft,
    wherein the first and second snap connections attach the first and second control wheel units, the housing frame, and the first and second shaft units to each other, and
    wherein the second snap connection is positioned intermediate the inner bearing element sleeve and the outer bearing sleeve.

20. An endoscope comprising:
    a handle comprising a housing frame and an outer bearing sleeve, the housing frame defining an interior of the housing and formed in one piece with the outer bearing sleeve, the outer bearing sleeve extending outwardly from the interior of the housing and including an inner bearing surface and a connection hole;
    a bending section; and
    a control system including:
    a first control wheel unit comprising a first wheel handle;
    a second control wheel unit comprising a second wheel handle;
    a first shaft unit comprising a first shaft connected to the first control wheel unit by a first snap connection;
    a second shaft unit comprising a second shaft having a central hole sized and shaped to receive therethrough the first shaft and defining an axial direction, the second shaft connected to the second control wheel unit by a second snap connection, the second shaft having an outer bearing surface bearing on the inner bearing surface of the outer bearing sleeve of the housing; and
    a center shaft having a portion thereof positioned within the second shaft,
    wherein the second control wheel is positioned between the first control wheel and the housing frame, the second shaft extends through the connection hole of the housing frame, and the first shaft extends through the connection hole of the housing frame and through the second shaft, wherein the first and second snap connections attach the first and second control wheel units, the housing frame, and the first and second shaft units to each other, wherein the second snap connection is positioned intermediate the center shaft and the outer bearing sleeve, and wherein the second shaft unit comprises a snap recess and a resilient projection configured to interlock with the snap recess.

21. The endoscope of claim 20, wherein the second snap connection is positioned intermediate the inner bearing element sleeve and the outer bearing sleeve.

22. An endoscope comprising:
a handle comprising a housing frame and an outer bearing sleeve, the housing frame defining an interior of the housing and formed in one piece with the outer bearing sleeve, the outer bearing sleeve extending outwardly from the interior of the housing and including an inner bearing surface and a connection hole;
a bending section; and
a control system including:
a first control wheel unit comprising a first wheel handle;
a second control wheel unit comprising a second wheel handle;
a first shaft unit comprising a first shaft connected to the first control wheel unit by a first snap connection;
a second shaft unit comprising a second shaft connected to the second control wheel unit by a second snap connection, the second shaft having an outer bearing surface bearing on the inner bearing surface of the outer bearing sleeve of the housing;
an inner bearing element sleeve positioned between the first shaft and the second shaft,
wherein the second snap connection is positioned intermediate the inner bearing element sleeve and the outer bearing sleeve,
wherein the second control wheel is positioned between the first control wheel and the housing frame, the second shaft extends through the connection hole of the housing frame, and the first shaft extends through the connection hole of the housing frame and through the second shaft, and
wherein the first and second snap connections attach the first and second control wheel units, the housing frame, and the first and second shaft units to each other.

\* \* \* \* \*